(12) United States Patent
Lutz et al.

(10) Patent No.: US 8,034,579 B2
(45) Date of Patent: Oct. 11, 2011

(54) PROTEINS WITH ENHANCED FUNCTIONALITY AND METHODS OF MAKING NOVEL PROTEINS USING CIRCULAR PERMUTATION

(75) Inventors: Stefan Lutz, Tucker, GA (US); Zhen Qian, Shanghai (CN)

(73) Assignee: Emory University, Atlanta, GA (US)

( * ) Notice: Subject to any disclaimer, the term of this patent is extended or adjusted under 35 U.S.C. 154(b) by 944 days.

(21) Appl. No.: 11/776,281

(22) Filed: Jul. 11, 2007

(65) Prior Publication Data

US 2008/0003619 A1 Jan. 3, 2008

Related U.S. Application Data

(63) Continuation-in-part of application No. PCT/US2006/004675, filed on Feb. 10, 2006.

(60) Provisional application No. 60/651,850, filed on Feb. 10, 2005, provisional application No. 60/696,325, filed on Jul. 1, 2005, provisional application No. 60/714,462, filed on Sep. 6, 2005, provisional application No. 60/726,009, filed on Oct. 12, 2005.

(51) Int. Cl.
*C12P 21/04* (2006.01)
*C12Q 1/34* (2006.01)
*C12N 9/20* (2006.01)

(52) U.S. Cl. ............... 435/18; 435/198; 530/350

(58) Field of Classification Search .......... 435/18, 435/198; 530/350
See application file for complete search history.

(56) References Cited

U.S. PATENT DOCUMENTS

| | | | |
|---|---|---|---|
| 5,635,399 A | 6/1997 | Kriegler et al. | 435/320.1 |
| 6,011,002 A | 1/2000 | Pastan et al. | 514/2 |
| 6,428,788 B1 | 8/2002 | Debinski et al. | 424/143.1 |
| 6,469,154 B1 | 10/2002 | Tsien et al. | 536/23.5 |
| 6,492,492 B1 * | 12/2002 | Stayton | 530/350 |
| 6,518,061 B1 | 2/2003 | Puri et al. | 435/320.1 |
| 6,699,687 B1 | 3/2004 | Tsien et al. | 435/69.1 |
| 6,831,158 B2 | 12/2004 | Nissen et al. | 530/397 |
| 7,060,793 B2 | 6/2006 | Tsien et al. | 530/350 |
| 2004/0175359 A1 | 9/2004 | Desjarlais et al. | |

OTHER PUBLICATIONS

European Search Report dated Nov. 1, 2008.
Ostermeier, et al., Evolution of Protein Function by Domain Swapping, Advances in Protein Chemistry 2000, vol. 55, 2000, pp. 29-77.
Lutz, S., "Engineering Lipase B from Candida Antarctica," Tetrahedron Asymmetry, Pergamon, Oxford, GB, vol. 15, No. 18, Sep. 20, 2004 pp. 2743-2748.
Beernink, P.T., et al., "Random Circular Permutation Leading to Chain Disruption Within and Near Alpha Helices in the Catalytic Chains of Aspartate Transcarbamoylase: Effects on Assembly, Stability and Function," Protein Science, Cambridge University Press, Cambridge, GB, vol. 10, Jan. 1, 2001, pp. 528-537.
Horlick, R.A., et al., "Permuteins of Interleukin 1 Beta-A Simplified Approach for the Construction of Permutated Proteins Having New Termini" Protein Engineering, Oxford University Press, Surrey, GB, vol. 5, No. 5, Jan. 1, 1992, pp. 427-431.
Ay, Jacqueline, et al., "Crystal Structures and Properties of De Novo Circularly Permuted 1, 3-1, 4-beta-glucanases" Proteins, vo. 30, No. 2, Feb. 1, 1998, pp. 155-167.
Quian, Zhen, et al., "Improving the Catalytic Activity of Candida Antarctica Lipase B by Circular Permutation" Journal of the American Chemical Society, American Chemical Society, Washington, DC., vol. 127, No. 39, Oct. 5, 2005, pp. 13466-13467.

* cited by examiner

*Primary Examiner* — Tekchand Saidha
(74) *Attorney, Agent, or Firm* — Emory Patent Group

(57) ABSTRACT

The present disclosure is relates to novel proteins and peptides having novel and/or enhanced functions and/or behaviors with respect to a native protein or peptide, and methods of making the novel proteins and peptides using techniques of circular permutation and protein engineering.

31 Claims, 13 Drawing Sheets

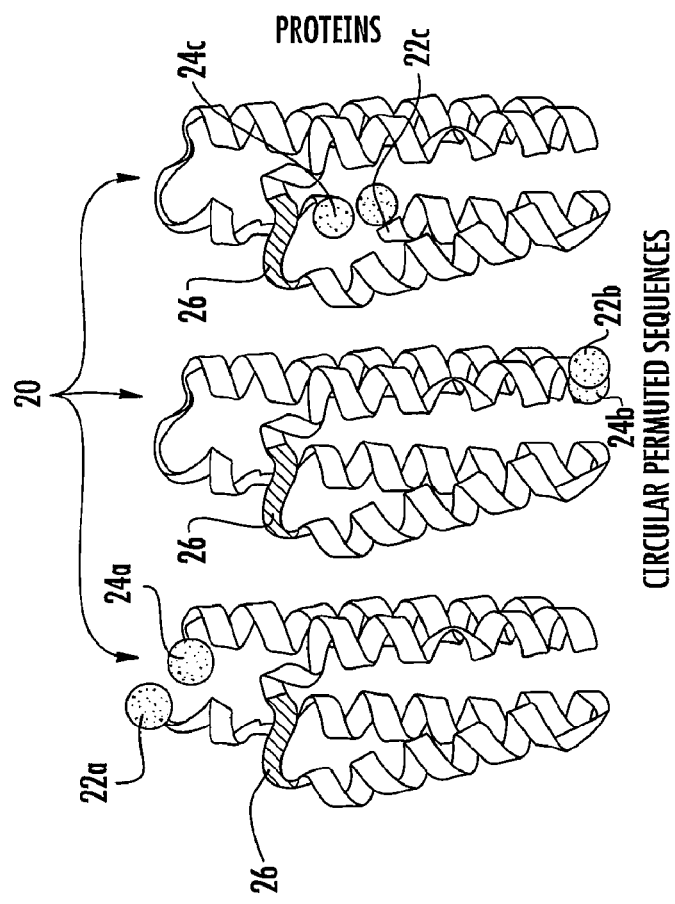
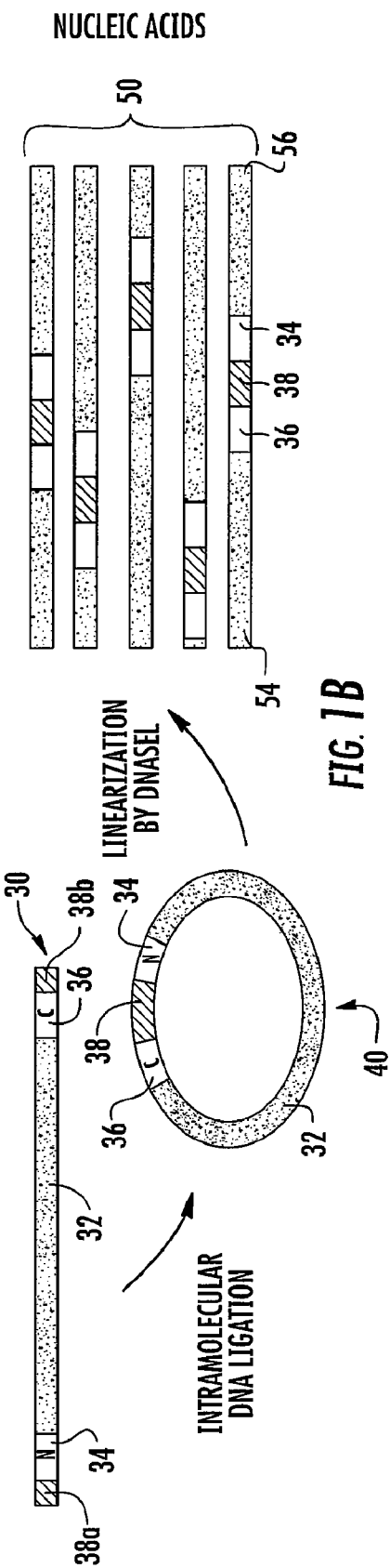
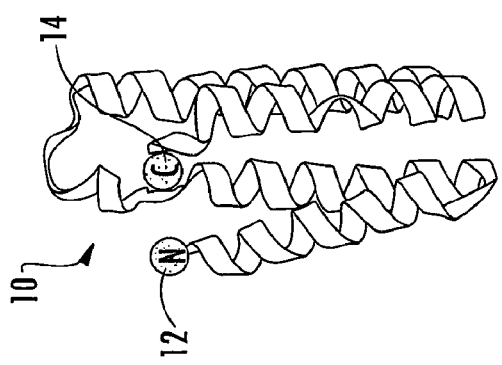
FIG. 1A
FIG. 1B

FIG. 12

Table 2. Apparent kinetic constants and enantioselectivity for wild type CALB and CALB variant cp283

| enzyme | substrate | $K_M$ (mM) | $k_{cat}$ (min$^{-1}$) | $k_{cat}/K_M$ (min$^{-1}$mM$^{-1}$) | E |
|---|---|---|---|---|---|
| wt | R-1 | 201 ± 19 | 620 ± 19 | 3.1 | 1.8 |
|  | S-1 | 251 ± 23 | 1396 ± 47 | 5.6 |  |
| cp283 | R-1 | 408 ± 50 | 797 ± 42 | 2 | 2 |
|  | S-1 | 457 ± 49 | 1807 ± 78 | 4 |  |
| wt | R-2 | 240 ± 36 | 8905 ± 568 | 37 | >40 |
|  | S-2 | n.d. | n.d. | <1* |  |
| cp283 | R-2 | 260 ± 39 | 31337 ± 1991 | 121 | >40 |
|  | S-2 | n.d. | n.d. | <3* |  |
| wt | R-3 | 845 ± 103 | 1635 ± 117 | 1.9 | >10 |
|  | S-3 | n.d. | n.d. | < 0.2* |  |
| cp283 | R-3 | 946 ± 75 | 2338 ± 110 | 2.5 | >15 |
|  | S-3 | n.d. | n.d. | < 0.2* |  |
| wt | R-4 | 238 ± 45 | 70 ± 6 | 0.3 | 5 |
|  | S-4 | 412 ± 37 | 24 ± 1 | 0.06 |  |
| cp283 | R-4 | 125 ± 27 | 86 ± 6 | 0.7 | 9 |
|  | S-4 | 354 ± 21 | 27 ± 1 | 0.08 |  |
| wt | R-5 | 182 ± 27 | 17 ± 1.2 | 0.1 | 25 |
|  | S-5 | 393 ± 50 | 1.4 ± 0.1 | 0.004 |  |
| cp283 | R-5 | 163 ± 33 | 64 ± 6 | 0.4 | 40 |
|  | S-5 | 402 ± 35 | 3.8 ± 0.2 | 0.01 |  | n.d.: not detectable; Values marked by asterisks represent estimates of maximum $k_{cat}/K_M$ values based on the GC instrument's detection limit. Enantiomeric ratio E = $k_{cat}/K_M$ (fast enantiomer) / $k_{cat}/K_M$ (slow enantiomer)

FIG. 13

Table 3. Stability and structure predictions based on CD data of selected CALB variants.

| enzyme | $T_M$ (°C) [a] | α-helical | β-sheet | turns [b] | unstructured |
|---|---|---|---|---|---|
| wild type | 53.5 ± 0.2 | 24% | 27% | 21% | 28% |
| cp144 | 46.2 ± 0.5 | 22% | 28% | 21% | 29% |
| cp148 | 49.9 ± 0.9 | 20% | 30% | 21% | 29% |
| cp150 | 48.7 ± 0.5 | 21% | 28% | 22% | 29% |
| cp268 | 37.6 ± 0.7 | 17% | 30% | 22% | 30% |
| cp277 | 34.1 ± 0.7 | 20% | 29% | 22% | 29% |
| cp283 | 39.9 ± 0.3 | 21% | 29% | 21% | 29% |
| cp284 | 39.8 ± 0.5 | 20% | 28% | 22% | 30% |
| cp289 | 41.5 ± 0.4 | 24% | 26% | 21% | 29% |

[a] $T_M$ values were determined by fitting CD ellipticity data at 222 nm to a two-state model, using Origin7 (OriginLab, Northhampton, MA). [b] Secondary structure composition was calculated using DICHROWEB (CONTINLL with SMP56 dataset).[17]

PROTEINS WITH ENHANCED FUNCTIONALITY AND METHODS OF MAKING NOVEL PROTEINS USING CIRCULAR PERMUTATION

CROSS-REFERENCE TO RELATED APPLICATIONS

This application claims the benefit of and is a Continuation-in-Part application of International Application No. PCT/US2006/004675, entitled "Novel Proteins with Enhanced Functionality and Methods of Making Novel Proteins Using Circular Permutation" filed on Feb. 10, 2006, which claims priority to copending U.S. provisional patent application Ser. No. 60/651,850, entitled "Lipase Variants from *Candida Antarctica*" filed on Feb. 10, 2005; Ser. No. 60/696,325, entitled "Lipase Variants from *Candida Antarctica*" filed on Jul. 1, 2005; Ser. No. 60/714,462, entitled "Circularly Permuted Proteins and Methods of Using Circular Permutation to Improve Protein Design and Activity" filed on Sep. 6, 2005; and Ser. No. 60/726,009, entitled "Circularly Permuted Proteins and Methods of Using Circular Permutation to Improve Protein Design and Activity" filed on Oct. 12, 2005, each of which are entirely incorporated herein by reference.

STATEMENT REGARDING FEDERALLY SPONSORED RESEARCH OR DEVELOPMENT

This invention was made with government support under grant number CHE-0404677 awarded by the National Science Foundation. The government has certain rights in the invention.

FIELD OF THE DISCLOSURE

The present disclosure is generally related to novel proteins and peptides having novel and/or enhanced functions and/or behaviors and methods of making the novel proteins and peptides.

BACKGROUND

Lipases play an important role in asymmetric biocatalysis. Their broad substrate specificity, generally high regio- and enantio-selectivity, as well as their ability to function in aqueous and organic reaction medium make them versatile tools for the kinetic resolution, derivatization, chiral synthesis, and polymerization of esters. Lipases can catalyze the formation, hydrolysis, and substitution (transesterification) of ester bonds, amid bonds, and the like. They are important biocatalysts in production of chiral building blocks for fine chemicals and pharmaceuticals, as well as in bulk products such as laundry detergent.

Suitable enzymes for a particular substrate can be identified by screening natural lipases or can be tailored by protein engineering. In the latter case, rational protein design, random mutagenesis, and DNA shuffling have generated laboratory catalysts with altered specificity, selectivity, and stability. However, very few natural and lab-made lipases show activity and enantioselectivity for bulky substrates such as esters of large secondary and tertiary alcohols. It has been hypothesized that the cause for the poor turnover of these substrates arises from steric constraints in the lipase active site, yet protein engineers have so far failed to generate improved biocatalysts. Tailoring these enzymes to novel, unnatural substrates is one of the primary challenges of protein engineering. Circular permutation may provide the ability to meet such challenges.

Circular permutation is a technique where the normal termini of a polypeptide are linked and new termini are created by breaking the backbone elsewhere. In many polypeptides, the normal termini are in close proximity and can be joined by a short amino acid sequence. The break in the polypeptide backbone can be at any point, preferably at a point where the function and folding of the polypeptide are not destroyed. Circular permutation creates new C- and N-termini, so the technique is often used in the creation of fusion proteins where the fused peptide or protein is attached at a different place on the host protein. For example, if the natural termini are at the interior of the base protein, it may be disruptive to attach a peptide or protein at the natural termini. By changing the attachment location to a place near the exterior of the host protein, stability of the host protein may be maintained.

Circular permutation provides an experimental way to investigate the biophysical consequences of backbone rearrangement or removal on ligand binding in ways not available using traditional deletion mutants. Circularly permuted proteins have been used previously to investigate the protein folding problem (Yang Y, et al. (1993) Proc Natl Acad Sci US. 90:11980-1984; Graf R, et al. (1996) Proc Natl Acad Sci USA 93:11591-11596). Both naturally occurring and synthetic circularly permuted proteins have been identified (Heinemann U, et al. (1995) Prog Biophys Molec Biol 64:122-143; Lindqvist Y, et al. (1997) Curr Opinion Struc Biol 7:422-427; Goldenberg D P, et al. (1983) J Mol Biol 164:407-413; Luger K, et al. (1989) Science 243-206-209). U.S. Pat. No. 5,635, 599 to Pastan et al. discloses fusion proteins created from circularly permuted interleukin 4 (IL4).

As mentioned above, circular permutants generally are created by disrupting the polypeptide chain at a selected point to create new termini and bridging the two natural termini either directly or through a linker such as an amino acid linker. Circular permutation thus has the effect of essentially preserving the sequence and identity of the amino acids of a protein, while generating new termini at different locations. Moreover, the tertiary structure of the protein is generally conserved. Circularly permuted proteins can be made chemically or created by recombinant techniques.

SUMMARY

Briefly described, embodiments of the present disclosure include novel proteins having novel or improved/enhanced functions or behavior. In embodiments of the present disclosure, the novel proteins are circularly permuted proteins having native amino-terminal and carboxy-terminal ends that have been linked, optionally with a linker sequence, and new amino-terminal and carboxy-terminal ends that are different from the native amino-terminal and carboxy-terminal ends of a corresponding native protein. In some preferred embodiments, the circularly permuted proteins include at least one improvement over the corresponding native protein. The improvement can include, but is not limited to, increased activity, increased accessibility to the active site, increased flexibility of the active site, increased the enantioselectivity, and broader and/or changed substrate specificity.

Embodiments of the circularly permuted proteins of the present disclosure also include circularly permuted proteins of the α/β-hydrolase fold family. The circularly permuted proteins of the α/β-hydrolase fold family include original amino-terminal and carboxy-terminal ends that have been linked, optionally with a linker sequence, and new amino-terminal and carboxy-terminal ends that are different from the original amino-terminal and carboxy-terminal ends of a corresponding native protein of the α/β-hydrolase fold family. In preferred embodiments, the circularly permuted protein of the α/β-hydrolase fold family include at least one improvement over the corresponding native protein, including but not limited to, increased activity, increased accessibility to the active site, increased flexibility of the active site, increased the enantioselectivity, and broader or changed substrate specificity.

Some embodiments of the circularly permuted proteins of the present disclosure and circularly permuted proteins of the α/β-hydrolase fold family also include at least one secondary mutation. In embodiments of the disclosure, the secondary mutation is selected from a deletion, insertion, or a substitution of one or more amino acids with different amino acids, or a combination thereof. The secondary mutation(s) result in a second circularly permuted protein. In preferred embodiments, the second circularly permuted protein has at least one improvement over the corresponding native protein and the corresponding circularly permuted protein. The improvements include, but are not limited to, increased activity, increased stability, broader or changed substrate specificity, increased active site flexibility, increased enantioselectivity, and combinations thereof.

The present disclosure also includes methods of making a novel protein of the α/β-hydrolase fold family. The methods include, but are not limited to, the following steps: selecting a native protein of the α/β-hydrolase fold family having an active site, an amino-terminal end, and a carboxy-terminal end; linking the amino-terminal and carboxy-terminal ends of the native protein to form a circular protein molecule; creating a library of circularly permuted proteins of the α/β-hydrolase fold family, where at least one circularly permuted protein in the library is a variant of the native protein having new amino-terminal and carboxy-terminal ends that are different from the amino-terminal and carboxy terminal ends of the native protein; selecting functional variants from the library; and testing selected functional variants for improvements with respect to the native protein. Such improvements include, but are not limited to, increased activity, increased accessibility, increased enantioselectivity, increased flexibility of the active site, increased stability, broader and/or changed substrate specificity, and combinations thereof.

Methods of the present disclosure also include methods of making a novel protein including the following steps: selecting a native protein having an active site, an amino-terminal end, and a carboxy-terminal end; linking the amino-terminal and carboxy-terminal ends of the native protein to form a circular protein molecule; creating a library of circularly permuted proteins, where at least one circularly permuted protein in the library is a variant of the native protein having new amino-terminal and carboxy-terminal ends that are different from the amino-terminal and carboxy terminal ends of the native protein; selecting functional variants from the library; mapping the location of the new amino-terminal and carboxy-terminal ends in the functional variants to determine locations of permissible permutations; selecting functional variants having new amino-terminal and carboxy-terminal ends located near a binding site of the protein; and testing selected functional variants for improvements with respect to the native protein, wherein the improvement is selected from: increased activity, increased accessibility, increased enantioselectivity, increased stability, and broader or changed substrate specificity.

The methods of making novel circularly permuted proteins of the present disclosure described above also include performing secondary engineering on one or more selected functional variants to produce at least one secondary circular permuted protein. In some embodiments, the secondary engineering include introducing at least one secondary mutation into the circularly permuted protein, where the secondary mutation includes, but is not limited to, deletion, insertion, and/or substitution of one or more amino acids of the circularly permuted protein, or a combination thereof. The secondary mutation(s) result in a second circularly permuted protein. In preferred embodiments, the second circularly permuted protein has at least one improvement over the corresponding native protein and the corresponding circularly permuted protein. The improvements include, but are not limited to, increased activity, increased stability, broader or changed substrate specificity, increased active site flexibility, increased enantioselectivity, and combinations thereof.

Other aspects, compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

The disclosure can be better understood with reference to the following drawings. The components in the drawings are not necessarily to scale, emphasis instead being placed upon clearly illustrating the principles of the present disclosure.

FIG. 1A illustrates the concept of circular permutation, showing a native protein structure on the left, and three circular permutants of the native protein on the right. FIG. 1B illustrates the process of circular permutation using recombinant DNA.

FIG. 9A shows the wild type CALB termini. FIG. 9B illustrates incremental truncation of the C-terminal tail in wild type CALB.

FIG. 12 illustrates Table 2.

FIG. 13 illustrates Table 3.

DETAILED DESCRIPTION

Figure 2C:
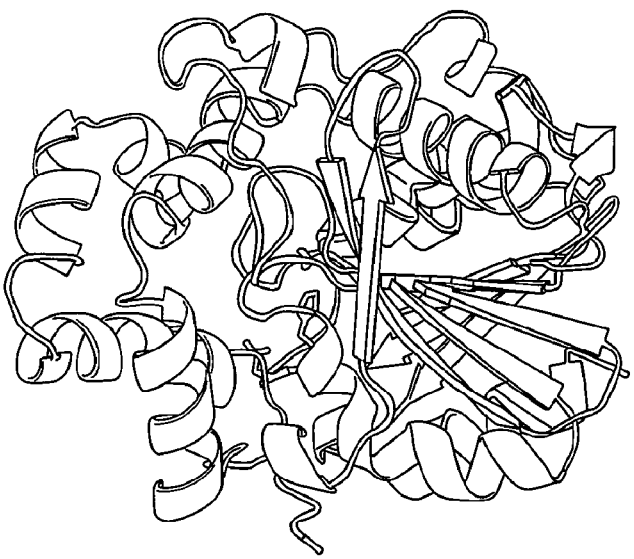
FIGS. 2B and 2C illustrate the secondary and tertiary structure of two members of α/β-hydrolase fold family, lipase B from *Candida antarctica* (CALB) and the epoxide hydrolase from *Agrobacterium radiobacter*, respectively.

Embodiments of the present disclosure will employ, unless otherwise indicated, conventional techniques of synthetic organic chemistry, biochemistry, molecular biology, and the like, which are within the skill of one in the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that unless otherwise indicated the present disclosure is not limited to particular materials, reagents, reaction materials, manufacturing processes, or the like, as such may vary. It is also to be understood that the terminology used herein is for purposes of describing particular embodiments only, and is not intended to be limiting. It is also possible in the present disclosure that steps may be executed in different sequence where this is logically possible.

It must be noted that, as used in the specification and the appended claims, the singular forms "a," "an" and "the" include plural referents unless the context clearly dictates otherwise. Thus, for example, reference to "a support" includes a plurality of supports. In this specification and in the claims that follow, reference will be made to a number of terms that shall be defined to have the following meanings, unless a contrary intention is apparent.

Definitions:

"Circular permutation," as used herein, refers to the process of taking a straight-chain molecule, fusing the ends (directly or through a linker) to form a circular molecule, and then cutting the circular molecule at a different location to form a new straight chain molecule with different termini. Circular permutation also includes any process that results in a circularly permutated protein, as defined herein. Circular permutation thus preserves the sequence and identity of the amino acids of a protein, while generating new termini at different locations.

The term "circularly permuted," "circularly permuted protein," and variations thereof as used herein refers to DNA, RNA and protein, essentially any linear molecule, in which the termini have been joined together, either directly or through a linker, to produce a circular molecule, and then the circular molecule is opened at another location to produce a new linear molecule with termini different from the termini in the original native/molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a protein or peptide, or a polynucleotide encoding such protein or peptide, is designated by the prefix "cp" (for "circular permutation") followed by the residue number of the amino acid where the N-terminus now resides in the circularly permuted polypeptide. Thus, the designation cp44 designates a circularly permuted protein in which the new N-terminus (e.g., in the position following the new opening site or where a peptide bond has been eliminated) is at amino acid 44 of the unpermuted or wild type protein.

The terms "unpermuted," "native," "wild type", or "unmodified" polypeptide, protein or enzyme, are used herein to provide a reference point for the polypeptide, protein, or enzyme prior to its rearrangement into a circularly permuted molecule, as described above. Typically, the unmodified, native, or wild type polypeptide, protein, or enzyme has an amino acid sequence that correspond substantially to the amino acid sequence of the polypeptide, protein, or enzyme as it generally occurs naturally or in vivo.

The term "linker" or "linker sequence," as used herein, refers to a molecule that is used to join the amino and carboxyl termini of a protein or its corresponding nucleic acid sequence (e.g. the RNA or DNA molecule encoding the protein). The linker is capable of forming covalent bonds to both the amino and carboxyl terminus. Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine). However, in a preferred embodiment, the linkers will be joined to the alpha carbon amino and carboxyl groups of the terminal amino acids. Another method for linking the wild type termini of a protein is the direct connection between the native amino and carboxylate moieties. The term "linker" may also refer to the nucleic acid sequence corresponding to the linking peptide sequence. In some embodiments, the circularly permuted protein is produced by linking the ends of the corresponding DNA or RNA sequence, forming various permutants by cutting the circularized nucleic acid sequence, and subsequently translating the nucleic acid sequences to form the circularly permuted protein(s).

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "opening site," as used herein when referring to circular permutation, refers to the position at which a peptide bond would be eliminated to form new amino and carboxyl termini. The opening site is designated by the positions of the pair of amino acids, located between the amino and carboxyl termini of the unpermuted (native) protein, that become the new amino and carboxyl termini of the circularly permuted protein.

As used herein, "polynucleotides" include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

A "nucleotide" refers to a sub-unit of a nucleic acid (whether DNA or RNA or analogue thereof) which includes a phosphate group, a sugar group and a nitrogen containing base, as well as analogs of such sub-units.

A "nucleoside" references a nucleic acid subunit including a sugar group and a nitrogen containing base. It should be noted that the term "nucleotide" is primarily used herein to describe embodiments of the disclosure, but that one skilled in the art would understand that the term "nucleoside" and "nucleotide" are interchangeable in most instances. One skilled in the art would have the understanding that additional modification to the nucleoside may be appropriate, and one skilled in the art has such knowledge.

A "nucleoside moiety" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. In addition, the term "variant" as used herein includes circular permutations of proteins and peptides.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (lie: Leu, Val), (Leu: Ile, Val), (Lys: Arg), (Met: Leu, Tyr), (Ser: Thr), (Thr: Ser), (Tip: Tyr), (Tyr: Trp, Phe), and (Val: lie, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a circularly permuted protein, with or without additional sequence alterations) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W, Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

An "enzyme," as used herein, is a polypeptide that acts as a catalyst, which facilitates and generally speeds the rate at which chemical reactions proceed but does not alter the direction or nature of the reaction.

As used herein, the term "promoter" includes all sequences capable of driving transcription of a coding sequence. In particular, the term "promoter" as used herein refers to a DNA sequence generally described as the 5' region of a gene, located proximal to the start codon. The transcription of an adjacent gene(s) is initiated at the promoter region. The term "promoter" also includes fragments of a promoter that are functional in initiating transcription of the gene.

A "primer" as used herein generally refers to a nucleic acid strand, or a related molecule, that serves as a starting point for replication, and are used in amplification techniques, such as the polymerase chain reaction (PCR). Primers used in such techniques are usually relatively short (generally about 20-50 base pairs), artificially synthesized polynucleotide strands. In PCR, primers are used to select the polynucleotide sequence to be amplified by the PCR process.

The term "expression" as used herein describes the process undergone by a structural gene to produce a polypeptide. It is a combination of transcription and translation.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce a nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

The term "transformation" refers to the introduction of DNA or RNA into cells in such a way as to allow gene expression.

The terms "native termini", "original termini" or "native terminus" refer to the terminal amino acid residues of a protein prior to its circular permutation (e.g., the amino and carboxy terminal ends of the native or wild type protein).

The terms "new termini" or "new terminus" refer to the terminal amino acid residues of a protein after its circular permutation. The "new termini" or "new terminus" are different from the native or original termini.

The term "coupled" as used herein refers to the binding, bonding, or other forms of association of a protein, specifically the association of a protein having an active site and a substrate or ligand.

As used herein, the term "enhance," "increase," and/or "augment" generally refers to the act of improving a function or behavior relative to the natural, expected or average. For example, a circularly permuted protein that has increased activity over that of the corresponding native protein, has improved activity (e.g. a faster rate of reaction, or binding/reacting with a greater number of substrates in the same amount of time) as compared to the activity of the corresponding native protein.

The term "substantially similar" as used herein generally refers to a function, activity, or behavior that is close enough to the natural, expected, or average, so as to be considered, for all practical purposes, interchangeable. For instance, a protein with substantially similar activity would be one that has an activity level that would not be considered to be substantially more or less active than the native protein.

As used herein, the term "improvement" or "enhancement" generally refers to a change or alteration in a function or behavior of a protein, such as an enzyme, that in the applicable circumstances is considered to be desirable.

The term "accessibility" as used herein refers to the ability of a substrate or ligand to associate with or couple the active site of a protein/enzyme. Thus, a protein with "increased accessibility" is one in which substrates (including natural or novel substrates) are more easily able to associate with or couple the active site of the protein, as compared with the native or wild-type protein.

The term "enantioselectivity" as used herein refers to process for interacting with a single desired enantiomer over others. Thus, a protein with "increased enantio-selectivity" has a greater preference for one enantiomer over the other enantiomer, as compared to what is natural or expected or to the native or another protein.

The term "substrate specificity" refers to the range of substrates that a polypeptide can act upon to produce a result. The term "broader substrate specificity" refers to a larger range of substrates that a polypeptide can act upon to produce a result, as compared to the native protein. The term "changed substrate specificity" refers to a different or altered range of substrates than a polypeptide can act upon to produce a result, as compared to the native protein.

A residue or terminus that is "in or near" the active site of a protein refers to a residue or terminus that is sufficiently close to the active site of the protein, when the protein is in its folded conformation, to affect the accessibility, flexibility, and/or functionality of the active site. The use of "in" or "near" are interchangeable.

The term "immobilized enzyme" refers to an enzyme bound covalently or non-covalently to the surface of a solid or semi-solid surface material (e.g., a matrix material) including, but not limited to, ion-exchange beads and agarose.

The term "reaction medium" refers to the environment in which the enzyme or immobilized enzyme catalyzes a chemical reaction. Typically, reaction medium for lipases and esterases, for example, include, but are not limited to, aqueous buffer solutions, organic solvents, and ionic liquids. Changes in the reaction medium are known to sometimes affect the properties of an enzyme, altering, for example, its substrate specificity and enantio-selectivity. Additional adjustable parameters of the reaction medium include, but are not limited to, the water activity in non-aqueous reaction medium, as well as the nature of the reagents in the chemical reaction including, but not limited to, vinyl acetate or acetic acid. In summary, optimization of the reaction medium for an enzyme-catalyzed reaction can be used to further improve the performance of enzymes.

The term "conformation" in reference to a protein or peptide (e.g. "folded conformation") generally refers to the higher folded states of the peptide beyond the primary structure (peptide sequence), particularly to the tertiary structure of the protein or peptide.

The term "secondary engineering" or "secondary mutation" refers to the act, or result thereof, of performing additional mutation, sequence alterations, or other protein engineering on a already mutated (e.g., non-native, non wild-type) protein. For instance, a circularly permuted protein already differs from the corresponding native protein in the location of its termini; thus, a secondary mutation of a circularly permuted protein would include another mutation or variation (e.g. a deletion, substitution, or insertion) from the native protein, in addition to the new termini location. Additional description and examples of secondary engineering and secondary mutations are discussed in greater detail below.

Description:

The present disclosure generally provides compositions including engineered proteins and peptides having increased activity and/or other enhancements/improvements over the corresponding native or wild-type proteins, where the amino-terminal and carboxy-terminal ends of the engineered proteins are relocated with respect to the amino-terminal and carboxy-terminal ends of the native protein, as illustrated in FIG. 1. In other words, the present disclosure provides compositions including active, or functional, circularly permuted proteins having higher or enhanced activity and/or other improvements over the native protein (e.g., increased accessibility, increased active site flexibility, increased enantioselectivity, increased stability, and broader and/or changed substrate specificity).

In one embodiment, the present disclosure provides circularly permuted proteins having the N and C-termini relocated to a location in or near the active site of the protein. As discussed further below, conventional thought in the art of circular permutation for protein design dictates that the new N and C-termini of a circularly permuted protein should not generally be in a location near the active site and generally should not be in a location known to form a part of an important secondary structure or tertiary fold of the protein. This is due to valid concerns that breaking the protein backbone at such a location could interfere with the folding and conformation, and thus the function, of the protein, possibly to the extent of inhibiting all functionality.

However, the compositions and methods of the present disclosure demonstrate that circularly permuted proteins having the termini relocated to certain locations in or near the active site of a protein, not only do not destroy functionality, but can even enhance functionality of the protein, in some cases up to about 175-fold, over the native protein. Moreover, the new amino-terminal and carboxy-terminal ends of such enhanced-function, circularly permuted proteins may be located not just in external loop regions near the active site of the protein, but also may be embedded in secondary structures such as alpha helices, which are near or form a part of the active site of a protein. In some embodiments the new amino-terminal and carboxy-terminal ends of the circularly permuted proteins are located within about 20 Å from the active site of the circularly permuted protein; in other embodiments the new termini are located within about 15 Å from the active site of the circularly permuted protein.

In other embodiments, the present disclosure provides circularly permuted proteins having the N and C-termini relocated to a location not in or near (e.g., distant from) the active site of the protein. Although the new termini are not in or near the active site of the protein, preferably the new locus has a desirable effect on protein function and/or behavior.

The present disclosure also provides libraries of circularly permuted proteins corresponding to a native protein of interest. The circular permutation libraries of the present disclosure include one or more variants of a protein of interest having relocated amino-terminal and carboxy-terminal ends, where the relocated ends are in a different location from the terminal ends of the native protein. Preferably, such libraries include circularly permuted variants having new terminal ends at locations throughout the polypeptide sequence. More preferably, such libraries include and can be screened for functional variants. Most preferably, such libraries include functional variants having increased activity or other improvements over the native protein. In some embodiments, the libraries include functional variants having new terminal ends at locations in or near the active site of the protein.

In some embodiments, the circularly permuted proteins of the present disclosure are proteins of the α/β-hydrolase fold family (e.g., lipases, esterases, acetylcholinesterase, dienelactone hydrolase, thioesterase, serine carboxypeptidase, proline iminopeptidase, proline oligopeptidase, haloalkane dehalogenase, haloperoxidase, epoxide hydrolase, and hydroxynitrile lyase). Many lipases and esterases have similar structures and/or functions. As such, some references refer to some lipases as esterases and vice versa. It is the intent of this disclosure to include all proteins of the α/β-hydrolase fold family, some of which may be called lipases and esterases, but the exact term of lipase or esterase may be interchangeable in some embodiments (e.g., proteins from *Candida antarctica* may be called lipases or esterases). Therefore, reference to lipase does not necessarily exclude esterase.

Lipases can catalyze the formation, hydrolysis, and substitution (transesterification) of ester bonds, amid bonds, and the like. They are important biocatalysts in production of chiral building blocks for fine chemicals and pharmaceuticals, as well as in bulk products such as laundry detergents. In particular in the context of kinetic resolution and chiral synthesis, the enzymes' broad substrate specificity, their high stability (e.g. tolerance of organic solvents and elevated temperatures), as well as their high enantio and regio-selectivity makes them popular choices.

Figure 2B:
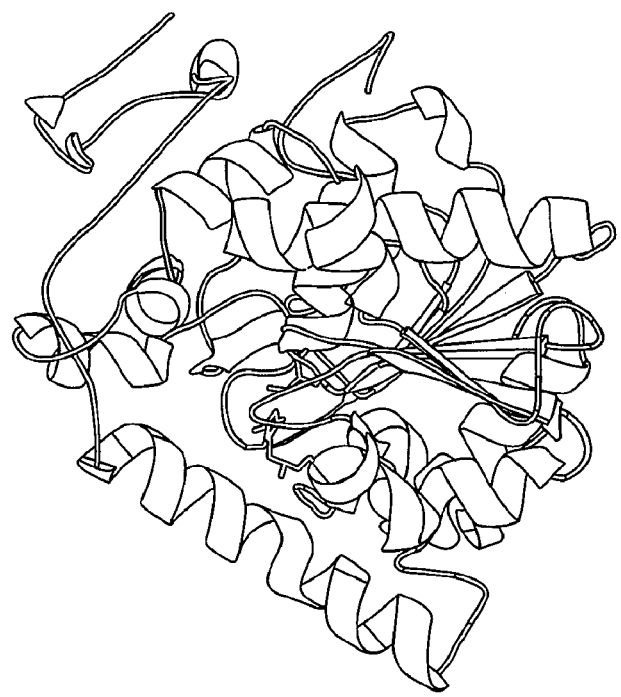

In preferred embodiments, the circularly permuted α/β-hydrolase fold family proteins or peptides (e.g., lipase) have increased activity and/or one or more other improvements, including but not limited to, increased stability, increased accessibility to the active site, increased active site flexibility, broader and/or changed substrate specificity, and/or increased enantioselectivity, as compared to the native protein. In some embodiments the circularly permuted proteins of the α/β-hydrolase fold family have new terminal ends in or near the active site. In some embodiments the new termini are located within about 20 Å from the active site of the circularly permuted protein; in other embodiments the new termini are located within about 15 Å from the active site of the circularly permuted protein. In some preferred embodiments, the new terminal ends are located in the region known as the "cap" domain or cap region of a α/β-hydrolase fold family protein. The cap domain generally refers to the region of the protein forming a cap-like structure over the active site that may form part of the active site binding pocket, but that does not generally form part of the core α/β-hydrolase fold. FIG. 2 depicts two members of the α/β-hydrolase fold family, lipase B from *Candida antarctica* (CALB) (FIG. 2B) and the epoxide hydrolase from *Agrobacterium radiobacter* (FIG. 2C). As can be seen from the figure, both proteins contain the core α/β-hydrolase fold, a cap region, and the active site (with the three residues of the catalytic triad) located generally between the core and the cap regions. In other embodiments, the circularly permuted α/β-hydrolase fold family have new terminal ends outside of or distant from the active site of the α/β-hydrolase fold family.

Although not intending to be bound by theory, in some embodiments of the present disclosure, the circularly permuted α/β-hydrolase fold family protein has broader and/or changed substrate specificity resulting from increased flexibility and/or accessibility of the active site allowing the α/β-hydrolase fold family to couple or associate with substrates and/or ligands that it is normally unable to couple. Such substrates include, but are not limited to, amides, esters, and particularly esters of large secondary and tertiary alcohols.

The reaction medium represents another parameter in the performance of individual enzymes in biocatalysis. While the specific effects of the environment on the catalysts are, for the most part, poorly understood, the results from stochastic approaches clearly demonstrate that the optimization of the reaction medium can affect the substrate specificity and enantioselectivity, as well as the protein stability. Reaction medium engineering typically involves two aspects: a) the modification of the enzyme catalyst itself, and b) the change of the reagent and solvent environment. Although not intending to be bound by theory, in the former, the enzyme can, for example, be used in its native form, be modified by chemical reactions of (most likely) surface residues to improve its solubility (for example nitration), or be immobilized on solid or semi-solid support (e.g. a matrix material, such as beads, or a column). Although not intending to be bound by theory, in the latter case, the choice of aqueous buffer solutions, organic solvents, and ionic liquids and temperature not only affects the nature of the chemical reaction (hydrolysis versus esterification) but is known to be able to affect the properties of an enzyme, altering, for example, its stability, substrate specificity and enantioselectivity. Additional adjustable parameters of the reaction medium include, but are not limited to, the water activity in non-aqueous reaction medium, as well as the nature of the reagents in the chemical reaction including, but not limited to, vinyl acetate or acetic acid. In summary, optimization of the reaction medium for an enzyme-catalyzed reaction can be used to further improve the performance of enzymes.

Figure 6:
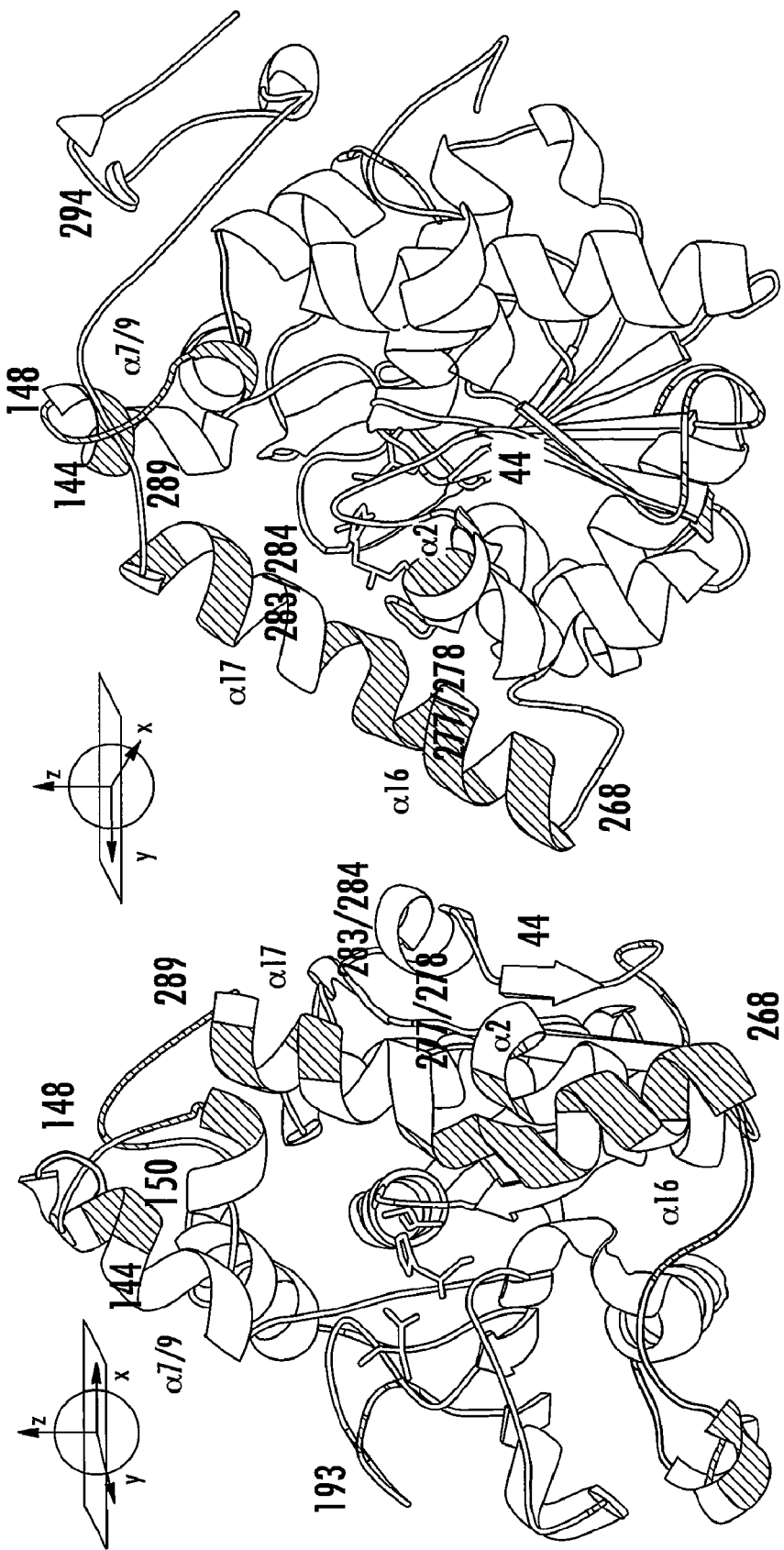
FIG. 6 illustrates the structure of CALB and identifies the locations of permissible permutation sites (indicated by hatched areas) and the variants selected for further characterization (indicated by amino acid location of the new amino terminus).

Among the most commonly used biocatalysts in the lipase family is lipase B from *Candida antarctica* (CALB) (ONA Sequence, SEQ ID NO: 1). CALB is a 317 amino-acid protein (SEQ ID NO: 2) with the characteristic α/β-hydrolase fold as its core structure and the catalytic triad Ser-His-Asp in the active site. A three dimensional representation of CALB, illustrating the protein's secondary and tertiary structure, is shown in FIG. 6. CALB shows outstanding specificity and selectivity, especially for esters of secondary alcohols. Recent protein engineering efforts have only added to the wide variety of reactions catalyzed by this enzyme. Thus, embodiments of the present disclosure provide circular permutations of CALB. Certain embodiments provide that the circularly permuted CALB has new amino- and/or carboxy terminal ends located in α17, α16, α9, α7, or α2 (e.g., between residue 44 and residue 47 of α2). Embodiments of the present disclosure include circularly permuted CALB proteins having new amino-terminal ends in locations including, but not limited to, residues 44, 144, 148, 150, 193, 268, 277, 278, 283, 284, 289, and 294. Circularly permuted proteins will be denoted herein by the prefix "cp-" and followed by the residue number that is the new amino terminus, for example, a circularly permuted protein with the new N-terminus as residue 144 would be denoted as cp144. In some preferred embodiments, the new termini are located in the cap region of CALB (e.g., the region including α7, α9, α17, α19 and any connecting external loop regions). In a preferred embodiment, the circularly permuted CALB has a new amino-terminal end located at residue 283 (cp283).

The present disclosure also provides methods of using circular permutation to design novel proteins, specifically enzymes, more specifically members of the α/β-hydrolase fold family, most specifically lipases and esterases, with enhanced activity and/or one or more other improvements over the native protein including, but not limited to, increased stability, increased accessibility to the active site, increased active site flexibility, broader and/or changed substrate specificity, increased enantioselectivity or a combination thereof. In some embodiments the improvement is due to increased flexibility and/or accessibility added to the active site due to changing the location of the termini to a location in or near the active site of the protein. It is also contemplated that changing the location of the termini to a location distant from, or otherwise outside of, the active site of the protein could also affect the conformational environment, or other aspect, of the protein in such a way so as to result in one or more of the above improvements.

Briefly described, the methods of the present disclosure include, but are not limited to, selecting a native protein having an active site, an amino-terminal end and a carboxy-terminal end; linking the amino-terminal and carboxy-terminal ends of the native protein to form a circular protein molecule, preferably via a linker; creating a library of circularly permuted proteins having at least one, but preferably multiple, circularly permuted protein in the library with a new amino-terminal end and carboxy-terminal end, which are different from the amino-terminal and carboxy-terminal ends of the native protein; and selecting functional variants from the library. The method may further include mapping the location of the new amino-terminal and carboxy-terminal ends in the functional variants to determine locations of permissible permutations and selecting functional variants with termini in various different locations for further testing. Such further testing may include, but is not limited to, detailed kinetic analysis, enantioselectivity, substrate specificity, and structural analysis (e.g., via fluorescence spectroscopy, circular dichroism, and protein engineering). Additionally, the methods of the present disclosure may further include selecting, from the library of functional variants, circularly permuted proteins having amino-terminal and carboxy-terminal ends located in or near a binding site of the protein, and then submitting such variants to further testing as described above. These methods will be described in greater detail in the discussion and examples below.

Using the methods of the present disclosure to introduce additional flexibility to the protein, especially in the region of the active site, allows researchers to design proteins and peptides, especially enzymes, to have desired enhancements/improvements over the native protein. Examples of some possible enhancements include, but are not limited to, increased activity, increased accessibility, increased enantioselectivity, increased stability, and broader and/or changed substrate specificity. It should be noted that these enhancements may not be due or are only partially due to flexibility of the protein, and embodiments of the disclosure are not limited to this theory regarding flexibility.

In one embodiment of the method of the present disclosure, described briefly here and in greater detail in the examples below, a library of engineered variants of CALB was generated by random circular permutation of the wild type protein. In several variants the relocation of the protein's termini altered the biochemical and biophysical properties of the catalyst, resulting in novel and improved activity toward selected substrates in response to changes in the active site geometry, substrate/product binding affinities, and/or protein flexibility. Functional variants among the library members were identified and subjected to detailed studies of their biochemical and biophysical properties. These circularly permuted biocatalysts may find applications in kinetic resolutions, biotransformations, or as polymerization catalysts. Alternatively, these permutants can serve as templates for secondary protein engineering approaches.

The present disclosure also includes methods of further engineering the circularly permuted proteins of the present disclosure to produce a second generation of circular permuted proteins (second circularly permuted proteins) having secondary mutations (e.g. mutations and/or alterations resulting from secondary engineering efforts, in addition to the alterations introduced by the initial circular permutation). Such secondary mutations include, but are not limited to, deletions, insertions, and substitutions of one or more amino acids in the polypeptide sequence of the circularly permuted protein, and combinations thereof. The secondary mutations result in one or more second circularly permuted proteins that preferably have at least one improvement as compared to the corresponding native protein and the corresponding circularly permuted protein, which includes, but is not limited to, increased activity, increased stability, increased enantioselectivity, increased accessibility to the active site, increased active site flexibility, and broader and/or changed substrate specificity.

Secondary engineering approaches for introducing the secondary mutations include, but are not limited to, various techniques of protein engineering, such as mutations based on rational design and methods of directed evolution, such as insertion, deletion, or substitution of an individual position or multiple positions in the protein sequence by mutagenesis, homology-dependent recombination, homology-independent recombination, computational methods of directed evolution using algorithms (e.g., the SCHEMA algorithm). Secondary engineering techniques are known to those of skill in the art, and many of the techniques listed above are described in Lutz, S., et al., "Novel methods for directed evolution of enzymes: quality, not quantity," (2004) Current Opinion in Biotechnology, 15:291-297, which is hereby incorporated by reference.

Exemplary secondary engineering efforts include, but are not limited to, rational and random mutagenesis, (as described in Cadwell, R. C. & Joyce, G. F. (1992) *PCR methods and applications*, 2, 28-33; and Reidmann-Olsen, J. F. et al. (1991) *Methods in Enzymology*, 208, 564-586, which are hereby incorporated by reference), as well as in vitro and in vivo recombination based on sequence homology. Examples of such approaches include, but are not limited to, DNA shuffling (as described in Stemmer, W. P. (1994) *Proc Natl Acad Sci USA*, 91, 10747-10751; Stemmer, W. P. (1994) *Nature*, 370, 389-391; and Zhao, H., Giver, L., Shao, Z., Affholter, J. A. and Arnold, F. H. (1998) *Nat Biotechnol*, 16, 258-261, which are hereby incorporated by reference) and methods for engineering proteins independent of sequence homology (e.g., ITCHY & SCRATCHY and other methods as described in Ostermeier et al., "A combinatorial approach to hybrid enzymes independent of DNA homology" (1999) Nature Biotechnology, 17: 1205-9; Lutz et al. "Creating multiple-crossover DNA libraries independent of sequence identity" (2001) Proc. Natl. Acad. Sci. USA 98:11248-53; and Sieber et al. "Libraries of hybrid proteins from distantly related sequences" (2001) Nature Biotechnology 19:456-60, which are hereby incorporated by reference).

In embodiments of the methods of the present disclosure, circular permutation is performed on a protein of interest to generate a library of permutants with new termini. Then, functional variants are identified by screening for protein activity by methods known to those of skill in the art, such as colony screening for enzyme activity, examples of which are described in further detail in the examples below. The functional variants are then mapped to determine the locations of permissible permutations in the protein sequence that allow the protein to retain activity. Then, representative functional permutants having new termini at various locations in the protein sequence are chosen for further testing. In some embodiments, the representative permutants are tested for detailed kinetic analysis to determine the relative activity with respect to the native protein. This helps to identify permutants with increased activity over that of the native protein.

The circularly permuted proteins can then also be tested for structural integrity via various methods known to those of skill in the art including, but not limited to, fluorescence spectroscopy and circular dichroism, both of which are described in greater detail in the examples below. Structural analysis of the protein helps to determine what effects the new location of the termini have on the local or overall structure of the protein. This can help identify proteins that have greater accessibility to the active site and/or greater active site flexibility, which may explain a higher level of activity. Structural analysis can also help to identify possible targets for secondary engineering efforts, such as by identifying areas of the protein that may lead to structural instability.

The circularly permuted proteins can also be tested for enantioselectivity to determine if they retain or have improved enantioselectivity over the native protein. In preferred embodiments, the circularly permuted protein(s) will have at least substantially similar enantioselectivity to the native protein. Various permutants may also be tested to determine how circular permutation affects the specificity, selectivity, and promiscuity of the protein. For instance, tests can be performed to measure the kinetic properties of functional variants on various selected substrates. Preferably, the circular permutants are tested on substrates from three categories: 1) natural substrates to probe for retention of wild type specificity and selectivity, 2) unnatural substrates to test for novel activity, and 3) on substrates no typically associated with the particular type of protein or enzyme to investigate whether circular permutation can give rise to promiscuous activity.

In some embodiments, the permutants, or those of particular interest, are tested for stability, since stability is a factor in the performance of the protein in certain environments that might be relevant for possible commercial use. In some embodiments, the circularly permuted proteins are also coupled to a surface/substrate, such as a matrix, for some or all of the above testing. Such substrates are known to those of skill in the art, and some exemplary substrates are described in the examples below.

In one non-limiting embodiment of the present disclosure, described in greater detail below, lipase B from *Candida antarctica* (CALB) was circularly permuted and various circular permutants were subject to further analysis and testing as described above. Additionally, a circular permutant of particular interest was identified and subject to secondary engineering techniques to generate a library of secondary circularly permuted proteins containing secondary mutations. These secondary permutants were then tested for various functions and behaviors according to the methods of the present disclosure. Details of this exemplary embodiment of the disclosure are described in detail below along with a detailed discussion of circular permutation techniques.

The introduction of the new and powerful combinatorial protein engineering methods of this disclosure provide the ability to accelerate the discovery of tailored catalysts for specific, synthetic problems and environmental constraints, giving the methods of this disclosure the possibility to play a dominant role in the future of protein engineering.

Circular Permutation:

Circular permutation is a little-explored technique for the diversification of protein frameworks useful in designing new and/or improved proteins and peptides. As discussed in more detail below and illustrated in FIG. 1A, circular permutation involves the connection of a protein's 10 natural termini 12 and 14 by a linker 26, preferably a peptide linker, followed by the reintroduction of new termini 22 and 24 in another region of the protein framework to produce one or more circular permutants 20. The termini relocation may affect the structural integrity of the protein, changing its active site accessibility and flexibility, all factors affecting an enzyme's substrate recognition and turnover. While surface loop regions seem preferred choices for new ends, experimental studies, as described in the examples below, have demonstrated that termini in secondary structures and the core region of a protein are also possible. In one embodiment of the disclosure, a complete combinatorial library of circular permuted CALBs (FIG. 3) was generated in order to maximize the efficiency and information content of the experiments.

Circularly permuted proteins have been found naturally in various organisms, including viruses, bacteria, plants, and higher animals. They are derived from either posttranslational modification, gene duplication or from exon shuffling events. Concanavalin A, a circularly permuted form of favin, was the first reported permuted protein in eukaryotes formed by post-translational transposition and ligation within the initial polypeptide. Swaposin, which is a plant aspartic proteinase insert, is the circularly permuted form of saposin. In 1995 Russell and coworkers found that although swaposin is highly homologous to saposin with four helices and a disulphide bond in structure, the two N-terminal helices of saposin are swapped to the C-terminal in swaposin and connected by a polypeptide linker. cDNA analysis of swaposin revealed that circular permutation occurs on the gene level instead of through posttranslational modification. Circular permutation of natural proteins may be of functional importance. In case of swaposin, it was hypothesized that the movement of the termini may facilitate the insertion of the swaposin domain within the aspartic proteinase, taking advantage of the orientation difference between swaposin and original saposin domain.

Another example of circular permutation is the aldolase superfamily. Members of this superfamily share a common TIM barrel fold, which contains eight α/β motifs assembled in a circular arrangement. This structural character may assist the occurrence of circular permutation, and enzymes with high similarity in substrate specificities and reaction chemistries except for different active site locations were revealed. It is proposed that the active site flexibility may account in part for the further adaptation for new functions, which possibly gives an explanation to the functional diversity of the TIM barrel in nature.

In the laboratory, circular permutation was first carried out on bovine pancreatic trypsin inhibitor through chemical condensation. In 1989 the use of genetic engineering was first used to design circularly permuted anthranilate isomerase. The termini relocation may afford valuable information about the importance of the natural ends of the polypeptide chain in respect to tertiary structure and biological function. It is believed that critical structure elements can not be disrupted by a breakage in the backbone, while chain connectivity is believed to affect the transition state and the folding nucleus of a protein. An example of the impact of circular permutation on protein function is the fusion protein between interleukin 4 and exotoxin from *Pseudomonas*, where the simple back-to-back fusion of the two components deactivated the interleukin but function was restored upon reorganization of the fusion protein by circular permutation.

Compared to rational design approaches, random circular permutation provides a more comprehensive approach to study protein stability and the relationship between protein structure and catalysis. Rather than generating one permutation per experiment, a complete set of all possible termini relocations are generated in a single test tube and evaluated by high-throughput screening or selection methods. This methodology can be applied to numerous and varied proteins, and in particular to enzymes, to engineer proteins with improved function over their native counterparts. In an embodiment of the present disclosure, circular permutation was applied to the exploration of CALB's structural and functional diversity.

It will be appreciated that while circular permutation is described in terms of linking the two ends of a protein and then cutting the circularized protein, these steps are not actually required to create the end product. Thus, circularized permutations of a generic protein with any of the novel sequences disclosed herein refers to all proteins of such structure regardless of how they are constructed.

It is important to create a permutation that will retain the biological activity of the native form of the molecule. If the new termini interrupt a critical region of the native protein, activity may be lost. Similarly, if linking the original termini destroys activity, it is likely that no permutation will retain native biological activity. Thus, there are two preferred, but limiting, attributes of a candidate for the creation of an active circularly permuted protein: 1) termini in the native protein that are favorably located so that creation of a linkage does not destroy native biological activity; and 2) an "opening site" that exists where new termini can be formed without functionally disrupting a region critical for protein folding and desired biological activity.

Thus, in general, good candidates for circular permutation are proteins in which the termini of the original protein are in close proximity and favorably oriented. Where the termini are naturally situated close together, it is expected that direct fusion of the termini to each other or introduction of a linker will have relatively little effect. It has been suggested that in roughly one third of the known structures of globular proteins the termini are in relatively close proximity (Thorton et al. J. Mol. Biol., 167: 443-460 (1983)). However, because the linker may be of any length, close proximity of the native termini is not an absolute requirement.

In a preferred embodiment, it is desirable to use a linker that preserves the spacing between the termini comparable to the unpermuted or native molecule. Generally, linkers are either hetero- or homo-bifunctional molecules that contain two reactive sites that may each form a covalent bond with the carboxyl and the amino terminal amino acids respectively. Suitable linkers are well known to those of skill in the art and include, but are not limited to, straight or branched-chain carbon linkers, heterocyclic carbon linkers, or peptide linkers. The most common and simple example is a peptide linker that typically includes several amino acids joined through peptide bonds to the termini of the native protein. The linkers may be joined to the terminal amino acids through their side groups (e.g., through a disulfide linkage to cysteine). However, in a preferred embodiment, the linkers will be joined through peptide bonds to the alpha carbon amino and carboxyl groups of the terminal amino acids. In addition, direct linking of the native protein termini via a peptide bond is possible in some proteins.

Functional groups capable of forming covalent bonds with the amino and carboxyl terminal amino acids are well known to those of skill in the art. For example, functional groups capable of binding the terminal amino group include anhydrides, carbodimides, acid chlorides, activated esters, amides, and the like. Similarly, functional groups capable of forming covalent linkages with the terminal carboxyl include amines, alcohols, and the like. In a preferred embodiment, the linker will itself be a peptide and will be joined to the protein termini by peptide bonds.

Conventional thought indicates that circular permutation requires that the protein have an opening site where the formation of termini will not interrupt secondary structure crucial in the folding process or critical elements of the final conformation. This is based on the belief that, even if the three-dimensional structure is compatible with joining the termini, it is conceivable that the kinetics and thermodynamics of folding would be greatly altered by circular permutation if opening the circularized protein separates residues that participate in short range interactions crucial for the folding mechanism or the stability of the native state. Goldenberg, Protein Eng., 7: 493-495 (1989). Thus, current practice advises that opening sites be selected in regions of the protein that do not show secondary structure such as alpha helices, pleated sheets, barrel structures, and the like.

While it is true that the choice of an opening site is important to the protein activity, it is not always the case that the new termini cannot be located within secondary structure elements or near the active site of the protein without negatively affecting the function of the protein. In fact, the compositions of this disclosure preferably include proteins where the new termini are located in or near the active site, while still preserving or even enhancing, the activity of the protein, in order to confer greater flexibility or other desirable characteristics to the active site and the circularly permuted protein as a whole. In some preferred embodiments, the new termini are located within about 20 Å from the active site of the circularly permuted protein; in other embodiments the new termini are located within about 15 Å from the active site of the circularly permuted protein. In some embodiments, the new termini are located between about 5 Å and 20 Å of the active site, between about 5 Å and 15 Å, or between about 10 Å and 15 Å of the active site.

Circularly permuted proteins may be made by a number of methods known to those of skill in the art. These include chemical synthesis, modification of existing proteins, and expression of circularly permuted proteins using recombinant DNA methodology.

Where the protein is relatively short (e.g., less than about 50 amino acids) the circularly permuted protein may be synthesized using standard chemical peptide synthesis techniques. If the linker is a peptide it may be incorporated during the synthesis. If the linker is not a peptide, it may be coupled to the peptide after synthesis. Solid phase synthesis in which the C-terminal amino acid of the sequence is attached to an insoluble support followed by sequential addition of the remaining amino acids in the sequence is one method for the chemical synthesis of circularly permuted proteins. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984), which are incorporated herein by reference.

Alternatively, the circularly permuted protein may be made by chemically modifying a native protein. Generally, this includes reacting the native protein in the presence of the linker to form covalent bonds between the linker and the carboxyl and amino termini of the protein, thus forming a circular protein. New termini are then formed by opening the peptide bond and then joining the amino acids at another location. This may be accomplished chemically or enzymatically using, for example, a peptidase.

If the opening reaction tends to hydrolyze more than one peptide bond, the reaction may be run briefly. Those molecules having more than one peptide bond opened will be shorter than the full length circularly permuted molecule, and the latter may be isolated by any protein purification technique that selects by size (e.g., by size exclusion chromatography or electrophoresis). Alternatively, various sites in the circular protein may be protected from hydrolysis by chemical modification of the amino acid side chains, which may interfere with enzyme binding, or by chemical blocking of the vulnerable groups participating in the peptide bond.

In a preferred embodiment, circularly permuted proteins can be synthesized using recombinant DNA methodology, as illustrated in FIG. 1B. Generally this involves creating a DNA sequence 30 that encodes the circularly permuted protein 32 (including an original/native N-terminus 34 and C-terminus 36), and DNA sequences 38a and 38b encoding for the linker 38. The DNA sequence 30 is then circularized by intramolecular DNA ligation. The circularized DNA 40 is then cut and linearized by DNaseI. In preferred embodiments, the amount of DNaseI is minimized in order to achieve generally only one cut per DNA sequence. Cutting and linearization of the circular DNA sequences 40 produces one or more circularly permuted DNA sequences 50 having new ends 54 and 56, encoding new amino and carboxy termini, respectively, of the encoded circularly permuted protein. The resulting circularly permuted proteins can be expressed by placing the circularly permuted DNA sequences 50 in an expression cassette under the control of a particular promoter, expressing the protein in a host, isolating the expressed protein and, if appropriate, renaturing the protein.

DNA encoding circularly permuted proteins may be prepared by any suitable method, including, for example, cloning and restriction of appropriate sequences or direct chemical synthesis by methods such as the phosphotriester method of Narang et al. Meth. Enzymol. 68: 90-99 (1979); the phosphodiester method of Brown et al., Meth. Enzymol. 68: 109-151 (1979); the diethylphosphoramidite method of Beaucage et al., Tetra. Lett., 22: 1859-1862 (1981); and the solid support method of U.S. Pat. No. 4,458,066, all incorporated herein by reference.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences. Alternatively, subsequences may be cloned and the appropriate subsequences cleaved using appropriate restriction enzymes. The fragments may then be ligated to produce the desired DNA sequence.

In a preferred embodiment, DNA encoding the circularly permuted protein may be produced using DNA amplification methods, for example polymerase chain reaction (PCR). First, the segments of the native DNA on either side of the new terminus are amplified separately. For example, since the native protein sequence of CALB is 317 amino acids long and the opening site is between amino acids 37 and 38 respectively, the sequences representing codons 1 through 37 and 38 through 317 are amplified separately. The 5' end of the first amplified sequence encodes the peptide linker, while the 3' end of the second amplified sequence also encodes the peptide linker. Since the 5' end of the first fragment is complementary to the 3' end of the second fragment, the two fragments (after partial purification, e.g., on LMP agarose) can be used as an overlapping template in a third PCR reaction. The amplified sequence will contain codons 38-317, the linker, and codons 1-37. The circularly permuted molecule may then be ligated into a plasmid.

The circularly permuted proteins may be expressed in a variety of host cells, including, but not limited to, *E. coli*, other bacterial hosts, *Pichia pastoris, Saccharomyces cerevisia*, other yeast or fungi, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the disclosure can be transferred into the chosen host cell by well-known methods such as electroporation or calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant proteins can be purified according to standard procedures of the art, including ammonium sulfate precipitation, affinity columns, column chromatography, gel electrophoresis and the like (see, generally, R. Scopes, Protein Purification, Springer-Verlag, New York (1982), Deutscher, Methods in Enzymology Vol. 182: Guide to Protein Purification, Academic Press, Inc. New York (1990)). Substantially pure compositions of at least about 90 to 95% homogeneity are preferred, and 98 to 99% or more homogeneity are most preferred for applications. Once purified, partially or to homogeneity as desired, the polypeptides may then be used in any desired application.

One of skill in the art would recognize that after chemical synthesis, biological expression, or purification, the circularly permuted protein may possess a conformation substantially different than the native protein. In this case, it may be appropriate to denature and reduce the protein and then to cause the protein to re-fold into the preferred conformation. Methods of reducing and denaturing the protein and inducing re-folding are well known to those of skill in the art. (See, Debinski et al. J. Biol. Chem., 268: 14065-14070 (1993); Kreitman and Pastan, Bioconjug. Chem., 4: 581-585 (1993); and Buchner, et al., Anal. Biochem, 205: 263-270 (1992), which are incorporated herein by reference.) Debinski et al., for example, describe the denaturation and reduction of inclusion body proteins in guanidine-DTE. The protein is then refolded in a redox buffer containing oxidized glutathione and L-arginine.

One of skill would recognize that modifications could be made to the circularized protein without diminishing its biological activity. Some modifications may be made to facilitate the cloning, expression, or incorporation of the circularly permuted ligand into a fusion protein. Such modifications are well known to those of skill in the art and include, for example, a methionine added at the amino terminus to provide an initiation site, or additional amino acids placed on either terminus to create conveniently located restriction sites or termination codons. For example, in some embodiments, circularly permuted proteins will have an additional methionine (Met) at the amino terminus to provide an initiation site. Circularly permuted proteins may also contain additional elements for cloning purposes.

One of skill will recognize that other modifications may be made. Thus, for example, amino acid substitutions may be made that increase specificity or binding affinity of the circularly permuted protein, etc. Alternatively, non-essential regions of the molecule may be shortened or eliminated entirely. Thus, where there are regions of the molecule that are not themselves involved in the activity of the molecule, they may be eliminated or replaced with shorter segments that merely serve to maintain the correct spatial relationships between the active components of the molecule.

Design of Lipases:

The following describes some non-limiting examples of the present disclosure. It should also be noted that although scientific assertions are made regarding how and/or why certain observations occur, there is no intent to be limited to these scientific assertions or to be bound by theory.

In some exemplary embodiments of the present disclosure, circular permutation was used to explore the effects of altered active site accessibility and protein backbone flexibility on the catalytic performance of lipase B from *Candida antarctica* (CALB). CALB was chosen in part because it is a member of the α/β-hydrolase fold family, and its wide use as a biocatalyst in applications in biotechnology and organic synthetic chemistry.

Figure 2A:
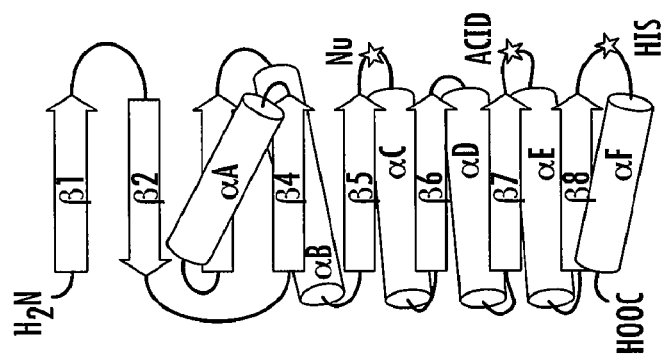
FIG. 2A illustrates a schematic of the secondary structural elements of proteins of the α/β-hydrolase fold family.

The α/β-hydrolase fold is one of the most versatile and widespread protein architectures and includes functionally diverse enzymes such as esterases, proteases, lipases, dehalogenases, haloperoxidases, lyases, and epoxide hydrolases. The structures of two members of the α/β-hydrolase fold family are illustrated in FIG. 2. Giving the fold its name, the common feature in these enzymes is a conserved eight-stranded mostly parallel α/β-structure (FIG. 2A) which arranges in a twisted β-sheet, flanked on both sides by α-helices (FIGS. 2B and 2C). The α/β-hydrolase fold, or core, provides a stable scaffold for the catalytic residues, typically a highly conserved triad. Beyond the conserved core structure, members of this fold show their evolutionary potential by accommodating a wide variety of loop insertions. Located mainly in the C-terminal half of the protein, these insertions can range from a few amino acids to entire domains, forming lids and caps that serve important roles by defining the substrate-binding pocket, and regulating accessibility of the active site.

A number of enzymes in this fold family play an important role as biocatalysts for asymmetric synthesis. Their broad substrate specificity and generally high regio and enantioselectivity makes the enzymes versatile tools for organic synthetic chemistry and biotechnology. Significant protein engineering efforts have been undertaken to customize these biocatalysts. Practitioners have adjusted the enzymes' thermostability and performance in organic solvents, as well as altered the substrate specificity and changed the enantioselectivity via rational design and directed evolution methods, but circular permutation has not been used with this family of proteins to engineer these enzymes.

CALB, a 317 amino acid-long enzyme, includes the α/β-hydrolase core structure, which includes the residues of the catalytic triad (S105, D187, H224), and an extended cap domain near the protein's C-terminus. CALB shows outstanding biocatalytic characteristics for the stereoselective conversion of primary and secondary alcohols and is a widely used biotransformation catalyst.

Construction of circular permutation libraries and identification of functional variants: Rather than substituting amino acids, it is believed that structural constraints in lipases could be relaxed through protein backbone cleavage. Specifically, it is believed that the internal relocation of a protein's N and C-termini in or near the active site can increase chain flexibility and active site accessibility, which could translate into higher activity for structurally more demanding substrates. Thus circular permutation was employed to explore the effects of termini relocation on a lipase's catalytic performance.

Using a combinatorial approach, circular permutation of CALB identified 63 unique functional protein permutants, and kinetic analysis of selected candidates indicated that a majority of enzyme variants either retained or surpassed wild type CALB activity on a series of standard substrates. Beyond the potential benefits of these tailor-made lipases as new catalysts for unnatural substrates, these results validate circular permutation as a promising general method for protein engineering, and in particular lipase engineering.

Given the difficulty of identifying suitable permutation sites by rational design, a comprehensive, combinatorial library of randomly permuted CALB variants was generated. Starting with wild type CALB gene, flanking oligonucleotide sequences were first introduced which encode for the flexible six-amino acid linker (-GGTSGG-) (SEQ ID NO: 3) to bridge the ~17 Å distance between the original termini. After intramolecular ligation, the circular DNA was linearized in random positions using DNaseI, as generally illustrated in FIG. 1B. Such methods are known to those of skill in the art and are described in the following, which are hereby incorporated by reference in their entirety: Baird, G. S., et al., *Proc. Natl. Acad. Sci. U.S.A.* 1999, 96, (20), 11241-11246; Beernink, P. T., et al., *Protein Sci.* 2001, 10, (3), 528-537; and Graf, R., et al., *Proc. Natl. Acad. Sci. U.S.A.* 1996, 93, (21), 11591-11596. Reaction conditions were chosen such that, on average, only a single cut per DNA strand was introduced.

Figure 3:
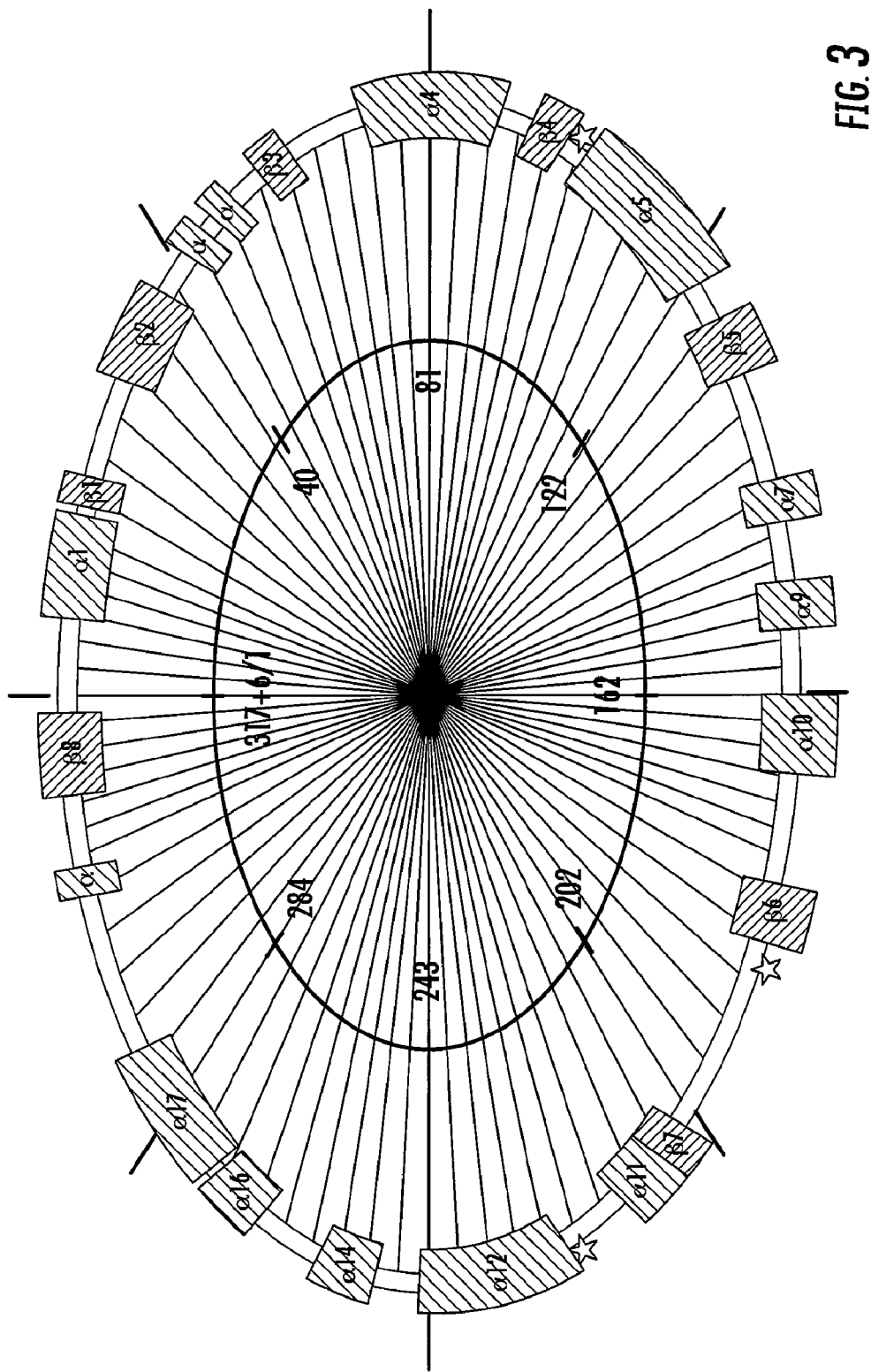
FIG. 3 is a circular permutation diagram of CALB illustrating the distribution of the termini location of 89 randomly chosen library members (outer circle) (library size ~$0.5 \times 10^6$).
Figure 4:
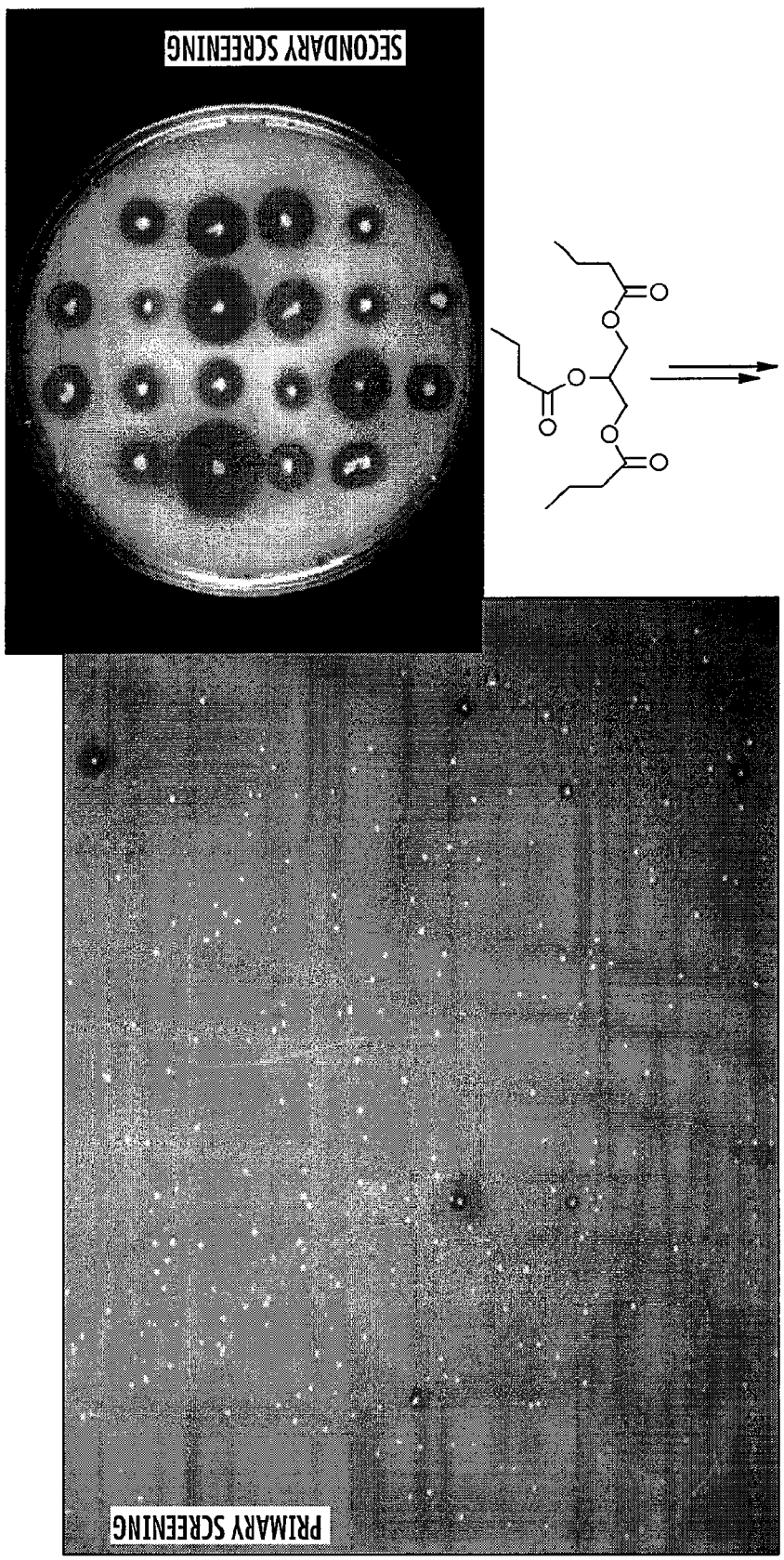
FIG. 4 shows the screening technique used to identify functional variants of the CALB library. Screening was performed on tributyrin plates to assess for hydrolase activity. Both a primary and secondary screening were performed, as illustrated.

The resulting library of CALB permutants was then cloned into pPIC9 and transformed into *Pichia pastoris* GS115 for protein expression as described in greater detail below. DNA sequence analysis of 96 randomly chosen members in the naïve library (~5×10⁵ colonies) confirmed the unbiased distribution of new termini over the entire length of the protein sequence, which is illustrated by the circular permutation map of CALB in FIG. 3. Next, functional variants in the CALB library were identified by colony screening on tributyrin plates as shown in FIG. 4 and described in greater detail in the examples below. The DNA sequence analysis of functional members identified 63 unique protein sequences with termini in positions other than wild type, which are shown as the lines in the outer circle on the circular permutation map of CALB shown in FIG. 5.

The data indicate that CALB tolerates permutations in numerous positions over the entire length of the protein. When mapped on the wild type CALB structure, the new termini of functional permutants coincide not only with surface loops but interrupt secondary structure elements on the enzyme's surface and interior regions as shown by the patterned regions in FIG. 6. Most noticeable is the concentration of functional permutations from amino acid 243 to 317, which make up the main portion of the enzyme's cap domain. This sequence is largely surface-exposed, wrapping around the front of the α/β-hydrolase core and forming the alcohol-binding portion of the active site pocket (α17).

Two additional regions tolerant to permutation include, but are not limited to amino acids 44 and 47, which are located in close proximity to the oxyanion-stabilizing residues and a cluster of permutations in α7/9 (amino acid 135 to 155). This second region constitutes the enzyme's lid region and is also a part of the cap domain. Two protein segments (residues 48-143 and 204-246) were identified with no functional permutation. These regions make up the core of the α/β-hydrolase fold and include residues S105 and H224 of the catalytic triad. It is believed that the absence of functional permutation near these residues, as well as the presence of only a single site proximal to the triad's third amino acid (D187) reflects this region's importance to catalysis and possibly its relevance to protein folding.

Kinetic analysis of protein variants: To examine the impact of circular permutation on catalysis eleven functional CALB variants with termini in or near the active site were selected for detailed kinetic characterization. The locations of the termini in these variants are shown on the structure of CALB in FIG. 6; the numbers correspond to the amino acid residue of the new terminus. Following overexpression in *P. pastoris*, the selected circularly permuted proteins were purified to homogeneity. The catalytic performance of these variants was determined in activity assays with two standard lipase substrates, measuring the initial rates of hydrolysis of the chromogenic substrate p-nitrophenol butyrate (pNB) and the fluorogenic substrate 6,8-difluoro-4-methylumbelliferyl (DiFMU) octanoate. The kinetic data are shown in Tables 1 and 2 below.

TABLE 1

Kinetic constants for CALB variants with p-nitrophenol butyrate (pNB).

| enzyme[a] | sequence[b] | $K_M(\mu M)$ | $k_{cat}$ (min⁻¹) | $k_{cat}$ (min⁻¹ µM⁻¹) | relative specificity[c] |
|---|---|---|---|---|---|
| wild type | L1/P317 | 410 ± 40 | 305 ± 10 | 0.74 | 1.0 |
| cp44 | G44/T43 | 690 ± 90 | 6 ± 0.5 | 0.01 | 0.01 |
| cp144 | His-L144/A141 | 550 ± 50 | 178 ± 7 | 0.32 | 0.4 |
| cp144a | L144/A141 | 820 ± 100 | 435 ± 28 | 0.53 | 0.7 |
| cp148 | His-A148/L147 | 500 ± 30 | 171 ± 4 | 0.34 | 0.5 |
| cp148a | A148/L147 | 550 ± 70 | 481 ± 29 | 0.87 | 1.2 |
| cp150 | His-S150/V149 | 510 ± 90 | 520 ± 45 | 1.02 | 1.4 |
| cp150 | S150/V149 | 425 ± 50 | 347 ± 16 | 0.82 | 1.1 |
| cp268 | P268/T267 | 580 ± 90 | 3051 ± 229 | 5.26 | 7.1 |
| cp277 | L277/A276 | 820 ± 100 | 1356 ± 94 | 1.65 | 2.2 |
| cp278 | L278/L277 | 1180 ± 160 | 3117 ± 269 | 2.64 | 3.6 |
| cp283 | His-A283/A283-KRPRINSP | 280 ± 50 | 2971 ± 180 | 10.61 | 14.3 |
| cp283a | A283/A282 | 410 ± 60 | 3251 ± 206 | 7.93 | 10.7 |
| cp284 | His-A284/A287-KRPRINSP | 550 ± 70 | 2980 ± 200 | 5.42 | 7.3 |
| cp284a | A284/A283 | 520 ± 80 | 4380 ± 298 | 8.42 | 11.4 |
| cp289 | His-P289/A284-KRPRINSP | 260 ± 30 | 3258 ± 215 | 12.53 | 16.9 |
| cp289a | P289/A288 | 790 ± 85 | 8055 ± 455 | 10.17 | 13.7 |
| cp294 | His-E294/A283 | 310 ± 40 | 73 ± 4 | 0.23 | 0.3 |

TABLE 2

Kinetic constants for CALB variants with 6,8-difluoro-4-methylumbelliferyl (DiFMU) octanoate.

| enzyme[a] | sequence[b] | $K_M(\mu M)$ | $k_{cat}$ (min⁻¹) | $k_{cat}$ (min⁻¹ µM⁻¹) | relative specificity[c] |
|---|---|---|---|---|---|
| wild type | L1/P317 | 2.6 ± 0.3 | 2 ± 0.1 | 0.8 | 1.0 |
| cp44 | G44/T43 | 5.6 ± 0.8 | 0.5 ± 0.05 | 0.1 | 0.13 |
| cp144 | His-L144/A141 | 2.0 ± 0.5 | 1 ± 0.1 | 0.5 | 0.6 |
| cp144a | L144/A141 | 3.0 ± 0.3 | 1.5 ± 0.1 | 0.5 | 0.6 |
| cp148 | His-A148/L147 | 3.5 ± 0.5 | 1.5 ± 0.2 | 0.35 | 0.4 |
| cp148a | A148/L147 | 6.1 ± 0.7 | 3.5 ± 0.2 | 0.57 | 0.7 |
| cp150 | His-S150A/149 | 2.7 ± 0.8 | 2.1 ± 0.2 | 0.8 | 1.0 |
| cp150 | S150/V149 | 5.5 ± 0.9 | 2.2 ± 0.2 | 0.4 | 0.5 |

TABLE 2-continued

Kinetic constants for CALB variants with 6,8-difluoro-4-methylumbelliferyl (DiFMU) octanoate.

| enzyme[a] | sequence[b] | $K_M(\mu M)$ | $k_{cat}$ (min$^{-1}$) | $k_{cat}$ (min$^{-1}$ $\mu M^{-1}$) | relative specificity[c] |
|---|---|---|---|---|---|
| cp268 | P268/T267 | 2.3 ± 0.3 | 28.8 ± 1.1 | 12.5 | 15.6 |
| cp277 | L277/A276 | 3.4 ± 0.5 | 16.3 ± 0.9 | 4.9 | 6.1 |
| cp278 | L278/L277 | 5.2 ± 0.8 | 49.9 ± 3.2 | 9.7 | 12.1 |
| cp283 | His-A283/A283-KRPRINSP | 2.5 ± 0.5 | 25 ± 1.4 | 10.9 | 13.6 |
| cp283a | A283/A282 | 2.4 ± 0.4 | 340 ± 17 | 140 | 175 |
| cp284a | A284/A283 | 2.2 ± 0.2 | 242 ± 8 | 112 | 140 |
| cp289 | His-P289/A284-KRPRINSP | 5.5 ± 1.0 | 120 ± 7 | 23 | 28.8 |
| cp289a | P289/A288 | 5.1 ± 1.0 | 150 ± 13 | 30 | 37.5 |
| cp294 | His-E294/A283 | 9.5 ± 2.0 | 2.6 ± 0.34 | 0.3 | 0.4 |

In Tables 1 and 2: [a]CALB nomenclature, e.g. cp44, indicates a circularly permuted protein whose N-terminus starts at amino acid 44 of the wild type sequence;
an "a" after the name indicates a variation of the particular cp-variant where tags and certain engineering artifacts (e.g., His tags, or C-terminal extensions) have been removed.
The sequence[b] indicates the N and C-terminal amino acids (all in single-letter code);
small variations in chain length of individual permutants are caused by reading frame shifts and staggered ends upon DNaseI digestion;
His indicates the presence of a His tag, and additional sequence fragments are also indicated by single letter code.
[c]Relative specificity = $k_{cat}/K_M$ (variant)/$k_{cat}/K_M$ (wild type).

The kinetic analysis confirmed that circular permutation has a significant impact on CALB's catalytic performance. The most substantial improvements in enzymatic activity over wild type CALB were observed upon termini relocation into the cap region of α16/17. Six of the seven variants (cp268-cp294) showed consistent improvements in their apparent $k_{cat}$'s for pNB and DiFMU octanoate. Three of the four variants (cp283, cp 284, cp289) show a consistent 10-fold improvement in their apparent $k_{cat}$'s for pNB and up to 175-fold increases in DiFMU octanoate turnover. Removal of the C-terminal peptide extension, an engineering artifact found in all three variants, and the His tag left catalytic rates generally unchanged or improved them, with a significant improvement in the case of cp283. In contrast, a removal of the entire protein fragment (amino acids 284-293) in cp294 appears detrimental to catalysis. Whether the deletion dismantles the active site pocket, preventing productive substrate binding, or affects protein stability as the disulfide-bond forming C293 is eliminated remains unclear.

The backbone cleavage in the lid region (cp144, cp148, cp150) showed moderate effects on hydrolysis of our test substrates. Both $K_M$ and $k_{cat}$ for all three variants stay within two-fold of the parent enzyme under the described assay conditions. Structure models predict close interactions of this protein region with the substrate's acyl portion. Furthermore, circular permutation of the lid region may alter the enzyme's response to changes in the reaction medium. The latter can affect lipase activity by modulating conformational changes in the lid region.

Finally, the kinetic data for cp44 shows a 10 to 100-fold reduction in relative specificity, compared to wild type CALB. The close proximity of the permutation site to the oxyanion-binding pocket likely results in the topological misalignment of the active site residues. Consistent with the observation of permutation-free protein segments, it is believed that protein permutation does increase local backbone flexibility. While such flexibility seems detrimental at positions in proximity to active site residues, the relaxation effects can be beneficial when applied to protein regions, which contribute to the active site topology but do not directly carry a side chain involved in catalysis.

In summary, CALB engineering by circular permutation has generated at least 63 new, unnatural lipase variants. Kinetic analysis confirmed that these protein variants can have sustained or improved catalytic function on multiple substrates over wild type, mutant, and shuffled CALBs. The observed rate enhancements are believed to result from improved active site accessibility and increased local protein backbone flexibility.

Analysis of substrate specificity and enantioselectivity in protein variants: To assess the circularly permuted CALB variants, three natural substrates were selected to probe for retention of wild type specificity and selectivity (e.g., compounds 1-3 below).

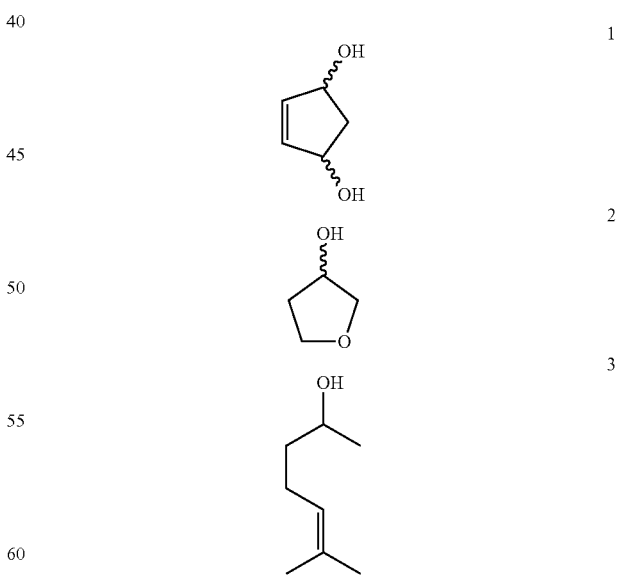

Three natural substrates for CALB, (1) 4-cyclopentene-1,3-diol 1; (2) 3-hydroxy-tetrahydrofuran; and (3) 6-methyl-5-hepten-2-ol, were tested as substrates for wild type CALB and cp283. The pure isomers of all three compounds are important chiral building blocks in organic synthetic chemistry, serving as starting materials for numerous pharmaceuticals. Additional compounds were also tested, and these studies are described in detail in Example 12 below and FIG. 11.

The experiments are typically performed in organic solvent, using immobilized enzymes and vinyl acetate as the second reagent, as described in Wang Y F, et. al, Lipase-Catalyzed Irreversible Transesterifications Using Enol Esters as Acylating Reagents—Preparative Enantioselective and Regioselective Syntheses of Alcohols, Glycerol Derivatives, Sugars, and Organometallics. *J Am Chem Soc* 1988, 110: 7200-7205, which is hereby incorporated by reference in its entirety. This reaction scheme has the advantage that the vinyl alcohol side product quickly rearranges into formaldehyde, effectively removing it from the reaction equilibrium and thereby avoiding product inhibition. Conversely, for reactions in organic solvents the enzyme is preferably immobilized. The CALB variants were immobilized on Lewatit VPOC 1600, a weak ion-exchange resin also used for commercial CALB products. In preliminary experiments, all three natural substrates 1-3 were acetylated by both the wild type CALB and cp283. Product analysis of reactions with 3 by chiral gas chromatography (Agilent 6850 GC equipped with CycloSil-B chiral column) showed faster esterification of substrate 3 by cp283 in comparison to wild type CALB. Equally important, the enantioselectivity was found uniformly high in both reactions.

Chiral tertiary alcohols and their esters (TAEs) are found in numerous natural products and represent valuable building blocks for organic synthetic chemistry. Their preparation by enzymatic kinetic resolution as an alternative to inadequate synthetic methods has been contemplated, yet the majority of lipases that are successfully employed for the separation of secondary alcohols show poor reactivity and at best mediocre enantioselective for TAEs. The enzymes' inferior performance on TAEs is believed to result from steric limitation within the active site of the catalyst. Structure comparison of lipases capable of hydrolyzing tertiary alcohols with non-active catalysts suggests a wider alcohol-binding pocket in the former which facilitates the binding of the larger tertiary group. The circular permutation methods of the present disclosure have identified new termini proximal to this binding site to test this hypothesis. Lipases capable of hydrolyzing tertiary alcohols also carry a distinctive GGGX loop as part of the active site, believed to maximize the flexibility of the oxyanion-stabilizing pocket. In summary, no biocatalyst with satisfying enantioselectivity and activity for even simple esters with tertiary alcohols have been reported in the literature.

Rational engineering attempts and directed evolution have not yielded a suitable catalyst either. While the studies have highlighted some of the underlying problems with the current lipases, little has been accomplished towards the exploration of new protein engineering approaches to redesign and extend lipase activity for tertiary alcohols. Although such conventional approaches have not produced mutants with the desired activity and selectivity, alterations of the active site binding pocket in permutated CALB of the present disclosure, or other permuted lipases and esterases according to the present disclosure, may be able accommodate these novel substrates.

Another potential application for these lipase variants is the synthesis of functional polymers. The high selectivity of CALB, together with its catalytic activity in aqueous and organic media has made the lipase an appealing polymerization catalyst. For example, the enzyme is utilized for the ring-opening polymerization of cyclic lactones such as the seven-membered ε-caprolactone. Of interest is the enzyme's limited capability to hydrolyze smaller ring systems such as δ-valerolactone and γ-butyrolactone, presumably caused by the higher rigidity of the ring that does not fit into the enzyme's active site. It is believed that circular permutation of the CALB can provide a catalyst with more flexibility in accommodating monomeric substrates, expanding the range of polymer-building blocks that can be utilized.

As the reorganization of the active site binding pocket as a result of the circular permutation is a possible mechanism for the generation of novel hydrolase activity, circularly permuted CALB variants may also have novel catalytic activity. Catalytic promiscuity in lipases and other α/β hydrolases have been reported, and thus alterations in the active site binding pocket as a result of circular permutation offer a very attractive mechanism for shifting enzyme substrate specificity.

Impact of circular permutation on protein structure and dynamics: The consequences of circular permutation on a protein's structural integrity and dynamics are not well understood, and little experimental work to that end has been described in the literature. The above-described data demonstrate that permutation can have a beneficial effect on the catalytic performance of CALB, yet the rational behind this observation is unclear. The data suggest that the new termini make significant contributions to catalysis and that the observed rate enhancements may not simply be attributed to faster product release alone. The preservation of enantioselectivity described above, as well as the minor changes in $K_M$ values in the variants shown in Tables 1 and 2 above, suggests that the substrate binding site remains largely intact despite the cleavage of the backbone.

Thus, circular permutation is believed to have consequences on the local protein environment. For example, cleavage of the peptide bond between amino acid 282 and 283 (cp283) may affect the local dynamics of the two smaller but defined helical regions, or the permutation may result in the "unraveling" of the helical regions, generating two disordered tethers. To study the impact of circular permutation on protein structure on a molecular level, a series of biophysical experiments based on circular dichroism and fluorescence spectroscopy were designed. These studies are complemented by secondary protein engineering of the CALB variants.

A protein's secondary structure content can be estimated by far UV CD spectroscopy. The spectra analysis of selected CALB variants listed in Table 1 and Table 2 shows little structural changes in permutants with termini in α7/9, as illustrated in the Far-UV circular dichrosim spectra of FIG. 7. In contrast, a clear decrease in the CALB variants' helical content is observed when the protein termini are located in a 16/17 as shown in FIG. 8. The decreases in mean ellipticity at 195 and 222 nm are indicative of reduced helical content in the enzyme variants. Furthermore, a correlation between the declining helical content and the position of the protein termini moving from cp289 to cp268 was noticed. These data suggest that elements of these helices which, upon permutation, shift to the N-terminus may not fold into a defined secondary structure. Such a trend of decreasing structural integrity is also consistent with separate CD thermodenaturation experiments shown as the inserts on FIGS. 7 and 8. Termini relocation from cp289 to cp268 shows a steady decrease in $T_m$ and a departure from a sharp two-state transition to less-cooperative protein unfolding.

In searching for an explanation for the destabilization of the N-terminal helix fragment, it was noticed that connecting the wild type termini with a six amino-acid linker forms of an extended loop near the amino terminus, as illustrated schematically in FIG. 9C. Large loops in proteins have been found to be thermodynamically unfavorable, decreasing the thermostability of model proteins. While the increased loop flexibility showed little changes in folding behavior of the protein, its effect on the free energy of the protein may be accounted for by the entropic cost of loop closure. Assuming that this loop region does not adopt secondary structure that could stabilize the protein, this model indicates the general trend in protein destabilization in connection with loop extensions. Thus, the CD results suggest that losses in secondary structure may accompany gains in catalytic activity of CALB. It is believed that these structural changes likely occur near the permutation site. Thus, this extended loop provided an interesting target for secondary engineering, as discussed in greater detail below.

Among the functionally selected CALB variants, permutants with new termini in α-helix 16 and 17 stand out in regard to the location of the backbone cleavage and the observed catalytic rate enhancements. As the kinetic data for cp294 show that deletions in that region can be detrimental to catalysis, the new termini likely play an important role towards enzyme function, yet it remains unclear whether the fragments of the cleaved helices retain their secondary structures or become unstructured tethers.

Fluorescence spectroscopy can be used to clarify the impact of circular permutation on the enzymes' structural integrity. Specifically, time-resolved fluorescence anisotropy experiments can be used to investigate the dynamics of the polypeptide chain at or near the cleavage site. Similar experiments on acetylcholinesterase have demonstrated that site-specific fluorophor labeling in the protein can be used to investigate the conformational changes upon substrate binding, as well as to probe the nano to microsecond dynamics of selected regions in the apo-protein. With these methods, the flexibility of fluorophors, attached to the side chain of a cysteine at or near permutation sites, can be measured. Serving as the "rigid" reference, the intact helix in wild type CALB provides little flexibility for labels, resulting in slow signal decays. In contrast, the labeled C293 residue in CALB(Δ301) (see FIG. 9) sits on a seven amino acid-long tether, minimizing conformational constraints and making it a reference for a highly flexible protein chain.

In order to attach fluorophor labels in α17, multiple surface-exposed positions were selected throughout the helix. For the second generation of mutants, three single cysteine mutants in positions A279, V286 and G288 have been created. These residues are located one or two helix turns away from the protein termini. As discussed below, the expression of properly folded and active enzymes with a free cysteine have been addressed in activity assays with the truncated enzyme CALB(Δ301), which has an unpaired cysteine, yet can be overexpressed in Pichia pastoris at wild type levels.

Secondary engineering of CALB variants: Based on the interpretation of the CD data, discussed above and shown in FIGS. 7 and 8, the possible connection between declining protein stability and the approximately 40 amino acid-long extended loop was tested by incremental truncation of wild type CALB (FIG. 9B) and cp283 (FIG. 9D).

To explore the functional necessity of the extended unstructured region in wild type CALB, a library of CALBs with incrementally truncated C-terminus (FIG. 9B) was created. A comprehensive library of C-terminal truncated CALBs was generated using ITCHY technology (Lutz S, Ostermeier M, Benkovic SJ: Rapid generation of incremental truncation libraries for protein engineering using alpha-phosphothioate nucleotides. *Nucleic Acids Res* 2001, 29:E16, incorporated herein by reference in its entirety) and underwent functional screening on tributyrin plates. Lipase genes from halo-forming colonies were analyzed by DNA sequencing. The results from this study show that the sixteen C-terminal amino acids of CALB can be removed without loss of lipase function. The shortest CALB variant, CALB(Δ301), is currently undergoing detailed kinetic and biophysical characterization. The truncation variants are named with respect to the location of the new C-terminus in the truncated peptide sequence; thus, CALB(Δ301) is a native CALB having its new C-terminus at amino acid 301 (where 16 amino acids from the C-terminal end have been removed).

Separately, CALB(Δ301) can serve as a reference for fluorescence anisotropy experiments described briefly above. As the truncation of the C-terminus removes C311, one of the natural six cysteines that form three disulfide bonds in the wild type enzyme, CALB(Δ301) is left with an unpaired thiol in position 293, making it unique labeling site in the flexible C-terminus. Protein overexpression data show no interference of the free C293 with the folding of the active truncated enzyme.

Figure 9:
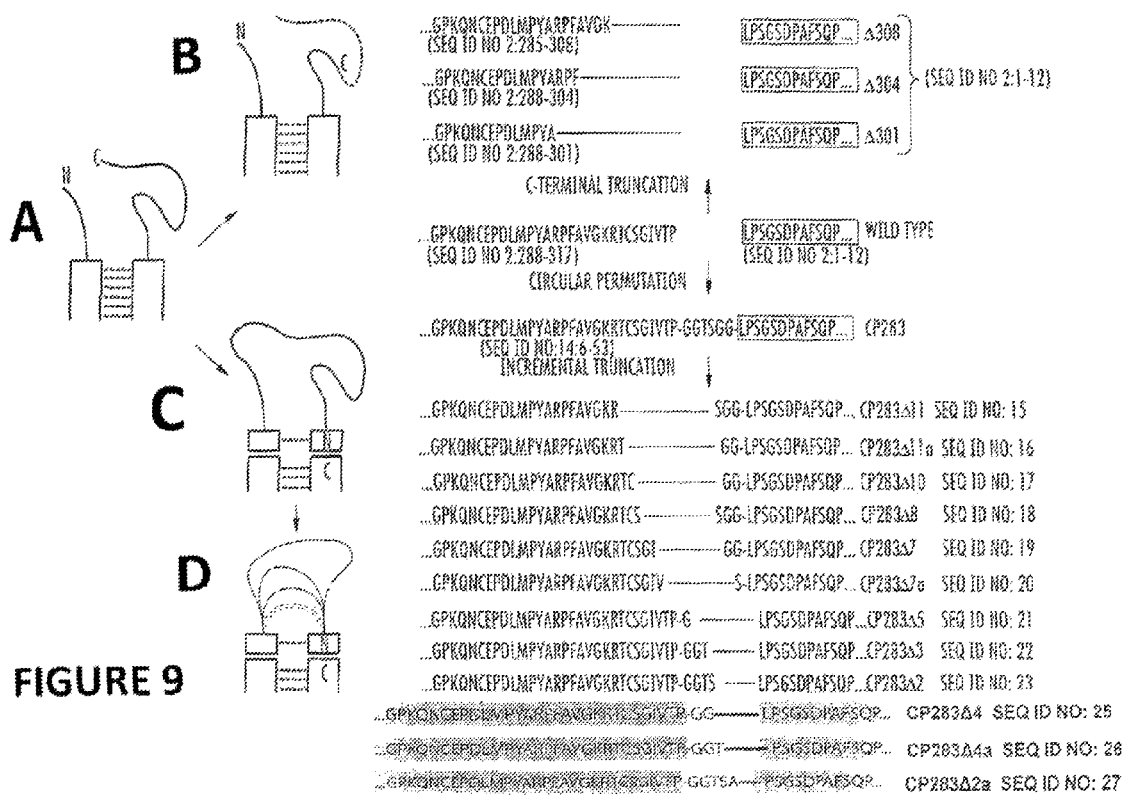
FIGS. 9A-B are schematic diagrams of the region representing the amino an carboxy-termini in native CALB and the location of the external loop in variant cp283.
FIG. 9C depicts the external loop in cp283.
FIG. 9D illustrates incremental deletions/truncations of the external loop structure in cp283. On the right-hand side of FIG. 9, several partial sequences corresponding to either wild type CALB (or C-terminal truncations thereof) or cp283 (or loop truncations thereof) are illustrated.

Separately, an incremental truncation experiment was performed to identify shorter versions of the newly created extended loop in cp283, which is shown schematically in FIG. 9D. Partial sequences, indicating the deleted amino acids, of several truncated variants of cp283 are also shown in FIG. 9. The cp/deletion variants are named with respect to the number of deleted amino acids. For instance, cp283 Δ11 indicates that the sequence is a variant of cp283 having 11 amino acids removed from the extended loop. The suffixes a, b, c, and so on, indicate different variants with the same number of deletions. Using CALB variant cp283 as template, a random library of ~3×10⁶ lipase variants was created using the ITCHY technology as described in Example 11. Functional screening of ~40,000 colonies identified numerous colonies with lipase activity, and DNA analysis has identified several active proteins with deletions of up to eleven amino acids in the loop. Subsequent overexpression and kinetic analysis of some of these protein variants has confirmed higher than wild type activity. For instance cp283Δ7a (as featured, in part, in SEQ ID NO: 20) was found to have increased activity over that of the native CALB.

Figure 10:
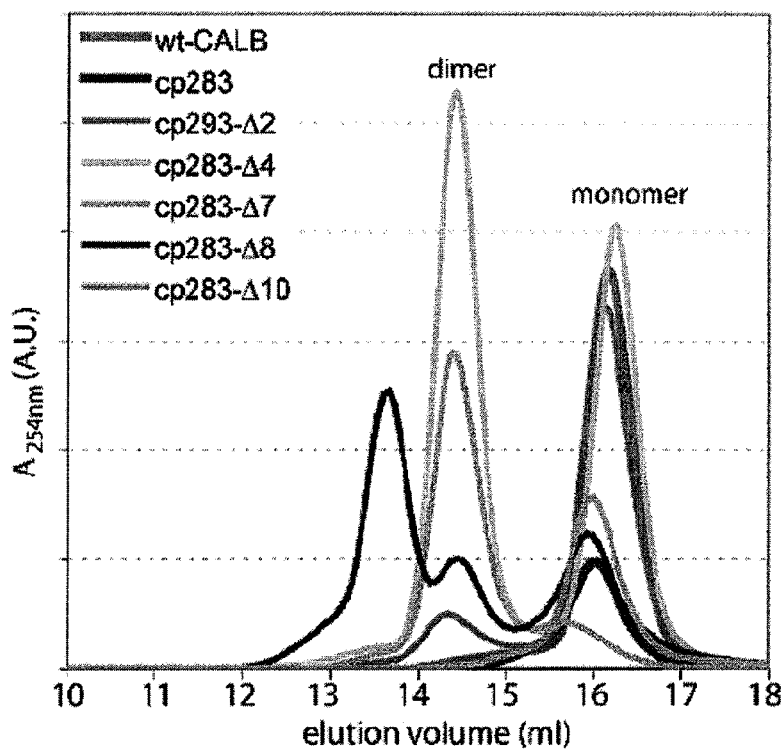
FIG. 10 is a graph illustrating gel filtration analysis of cpCALB variants.
Figure 11:
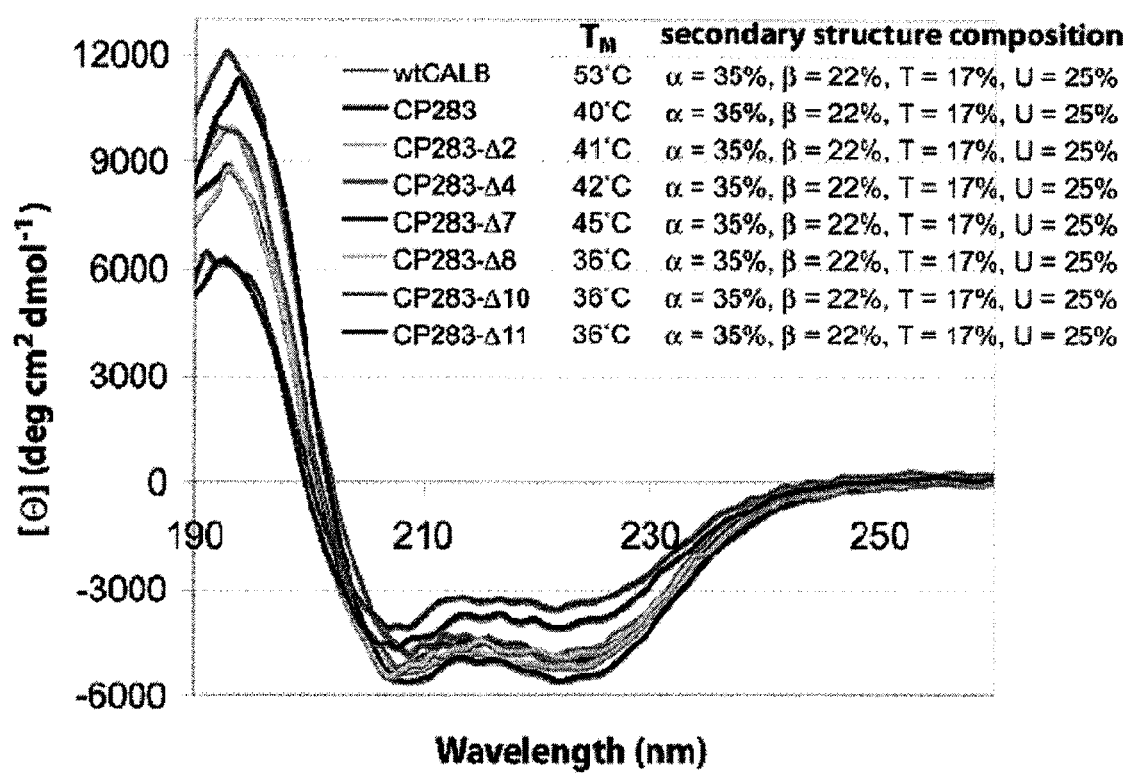
FIG. 11 is a graph illustrating an analysis of the secondary structure of the cpCALB variants.

In addition, analysis of these truncation variants of cp283 revealed that truncation of the loop affected dimerization of the CALB variant, which was related to stability, as described in Example 11 and illustrated in FIGS. 10 and 11. Some of the truncation variants were analyzed for secondary structure content and thermostability, as illustrated in FIG. 11. Variants cp283-Δ2 to Δ7 showed increasing $T_M$ and wild type-like secondary structure content, while variants cp283-Δ8 to Δ11 showed decreasing $T_M$ and loss of secondary structure content. Thus, it appears that truncations in the extended loop of CALB-283 results in more native-like secondary structure and increased stability, due at least in part to an increased ability to form dimers.

The methods described herein using the concept of circular permutation and optionally followed by secondary engineering may be applied to other lipases, esterases, hydrolases, and the other proteins and peptides and are not intended to be limited to the embodiment described herein or in the examples below.

EXAMPLES

The following detailed examples are given to illustrate some preferred embodiments of the present disclosure and are not intended to limit it in any manner.

Example 1

Materials

Chemicals: Fluorogenic substrate 6,8-difluoro-4-methylumbelliferyl octanoate (DiFMU octanoate) and the reference standard 6,8-difluoro-7-hydroxy-4-methylcoumarin (DiFMU) were purchased from Molecular Probes (Eugene, Oreg.). p-Nitrophenyl butyrate (p-NB) was purchased from Sigma (St. Louis, Mo.). Enzymes were purchased from New England Biolabs (Beverly, Mass.) unless noted otherwise.

Strains and media: *Pichia pastoris* GS115 (his4) (Invitrogen, Carlsbad, Calif.) was used for the lipase expression. *E. coli* strain DH5α-E(Invitrogen, Carlsbad, Calif.) was used for all vector constructions. *P. pastoris* was grown in YPG medium (10 g yeast extract, 20 g bacto peptone, 20 g glucose per liter). BMGY medium (10 g yeast extract, 20 g peptone, 13.4 g yeast nitrogen base, 0.4 mg biotin, 10 ml glycerol, and 100 ml 1 M potassium phosphate buffer, pH 6.0 per liter) and BMMY medium (10 g yeast extract, 20 g peptone, 13.4 g yeast nitrogen base, 0.4 mg biotin, 5 ml methanol, and 100 ml 1 M potassium phosphate buffer, pH 6.0 per liter) were used for protein expression. MD His⁻ plates were used for selection of transformants (13.4 g yeast nitrogen base, 0.4 mg biotin, 20 g dextrose, 15 g agar per liter). MM tributyrin plates were used to screen the lipase-secreting transformants (13.4 g yeast nitrogen base, 0.4 mg biotin, 5 ml methanol, 10 ml tributyrin, 15 g agar per liter).

Example 2

Construction of wt-CALB Expression Vectors

The wild type calB (wt-calB) gene SEQ ID NO: 1 (having protein sequence SEQ ID NO: 2) was isolated from *Candida antarctica* (ATCC strain #32657) by a two-step PCR amplification using the primers ZQ_CALBfor1 (5'-GAGGCTGAAGCTCATCATCATCATCATCATAG-CAGCGGCCTTGTTCCA CGT CTACCTTCCGGTTCGGACCCT-3') (SEQ. ID NO: 5), ZQ_CALBfor2 (5'-CGC CTCGAGAAAAGAGAGGCTGAAGCT CATCATCAT-CATCATCAT-3') (SEQ. ID NO: 6), and ZQ_CALBrev (5'-CGCGCGGCCGCTTAGGGGGTGACGAT GC CGGAGCA-3') (SEQ. ID NO: 7). The amplified gene included a (His)₆ tag followed by a thrombin cleavage site at the N-terminus of the lipase gene. Restriction enzyme recognition sites XhoI and NotI were also introduced into the 5' and the 3' ends respectively (recognition sequence underlined). The PCR product was digested with XhoI and NotI and ligated to the vector pPIC9 (Invitrogen, Carlsbad, Calif.) digested with the same restriction enzymes. This construct (pPIC9-calB) brought the CALB gene under the control of the methanol inducible alcohol oxidase promoter (AOX1) and in frame with the α-factor secretion signal peptide of *Saccharomyces cerevisiae*.

Example 3

Random Circular Permutation of calB

The wt-calB (SEQ ID NO: 1) was amplified by PCR using primers ZQ_cpCALBfor (5'-GGT ACTAGTGGTGGCCTACCTTCCGGTTCGGACCCT-3') (SEQ. ID NO: 8) and ZQ_cpCALBrev (5'-CGC ACTAGTACCGCCGGGGGTGA CGATGCCGGAGCA-3') (SEQ. ID NO: 9) harboring a SpeI site at both ends (underlined). After digestion with SpeI, 5 μg PCR fragment was circularized at a concentration of 2.5 ng/μl with 90 Weiss units T4 DNA ligase (Promega, Madison, Wis.) overnight at 16° C. This construct generated a circular calB with an 18-bp linker sequence (SEQ. ID NO: 4) that encodes Gly-Gly-Thr-Ser-Gly-Gly (SEQ. ID NO: 3) joining the natural N- and C-terminals. The linker designed consisted of a six-amino acid peptide, rich in glycine for flexibility and serine/threonine for hydrophilicity. After ethanol precipitation, the DNA was subjected to exonuclease III (0.4 units/μg DNA, Promega, Madison, Wis.) digestion at 37° C. for 30 min to remove remaining linear DNA. The exonuclease III was inactivated by heating at 65° C. for 15 min. The DNA was purified by QIAquick columns and eluted with 50 μl EB buffer.

Random relinearization of the circularized gene was performed by limited digestion with DNaseI (Roche, Indianapolis, Ind.) (RNaseI-free; 0.5 milliunits/μg DNA) in 50 mM Tris.HCl, pH7.5, 1 mM MnCl₂, DNA (5 μg/ml) at room temperature for 15 min. The reaction was stopped by adding 10 μl 0.5 M EDTA, and desalted by QIAquick columns (Qiagen, Valencia, Calif.) into elution buffer (10 mM Tris-HCl, pH 8.5). The linearized DNA was repaired using T4 DNA polymerase (Promega, Madison, Wis.) (1 unit/μg DNA) and T4 ligase (2 Weiss units/μg DNA) at room temperature for 1 h in T4 ligase buffer with the addition of dNTPs to a final concentration of 150 μM. The linearized and cured DNA was recovered by agarose gel electrophoresis.

Example 4

Creation of the pPIC9-cp-calB Library

The direct blunt-end ligation of cp-calB into the expression vector pPIC9 was difficult due to the vector's size. Successful library integration was instead achieved by using pAMB-CAT (Ambion, Austin, Tex.) as a shuttle vector. In preparation for library cloning, pAMB-CAT was modified to carry the N-terminal extensions (His tag, Thrombin cleavage site, start codon) upstream from the calB cloning site plus a stop codon immediately following the site of insertion. Therefore, PCR-amplified wild type calB (primers: ZQ_CALBfor1, ZQ_CALBfor2, ZQ_CALBrev) (SEQ. ID NOs: 5, 6, and 7, respectively) was digested with NotI/XhoI and ligated to the vector pAMB-CAT digested with the same restriction enzymes. The resulting vector was amplified using primers ZQ_pAMBfor (5'-CCG GATATCAGGCCTT GGAACAAG-GCCGCTGCTATG-3') (SEQ. ID NO: 10) and ZQ_pAMBrev (5'-CCG GATATCTTATAAGCGGCCGCAAGCTTGTCG-3') (SEQ. ID NO: 11), which harbored a StuI and a PsiI site (underlined) as well as EcoRV sites (dashed lines) flanking both ends. The amplified vector was digested with EcoRV and ligated with a segment generated from EcoRV digestion of pET-16b vector (Novagen, Madison, Wis.) to increase the size of the insert. This enabled subsequent digests to be monitored. Finally, the vector was digested with StuI and PsiI and the cp-calB library was incorporated into the vector by blunt-end ligation. Transformation of the plasmid into electro-competent *E. coli* DH5α-E cells generated the pAMB-cp-ca/B library (~5×10⁵ members). The colonies were harvested and the plasmid was isolated by QIAprep Spin Miniprep kit.

In a second cloning step, the cp-calB library was integrated in pPIC9. Purified pAMB-cp-ca/B was digested with NotI/XhoI and the segment containing the cp-calB library was ligated to the pPIC9 vector digested with the same enzymes. Approximately 1.5×10⁶ colonies were obtained after transformation into electro-competent *E. coli* DH5α-E cells. The transformants were harvested and the plasmid was isolated using the QIAprep Spin Miniprep kit.

The two-step protocol yielded libraries consisting of 500,000 members. Given the theoretical library size of 317+6 (protein length plus peptide linker), such library size virtually guaranteed that each member of the library was represented at least once. The absence of any detectable biases in the distribution of newly created protein termini was confirmed by DNA sequencing of 89 CALB genes of randomly picked library members (FIG. 3). In addition to the expected permuted full-length CALB genes, several library members that carried insertions and deletions of one or more residues of the wild type protein were identified. In some cases, the manipulation of the gene sequences by PCR also introduced additional sequence variation as a result of one or more nucleotide substitutions that can result in mutations of the original protein sequence.

Finally, an important aspect for the analysis of the CALB variants was the transformation of the single cp-CALB gene library member per host cell. In contrast to bacterial expression systems, *Pichia pastoris* incorporates the transformed plasmid and its content into its chromosomal DNA. While multiple integrations of a target gene per cell are advantageous for homogenous DNA samples, leading to higher expression levels, the same is not the case for libraries. The integration of multiple library members in a single host's DNA could dilute the functional properties of individual members. Further, host cells, which show lipase activity, would require extensive secondary characterization to isolate the functional variant(s) in the sequence pool. Various transformation protocols, known to those of skill in the art, can be used. In the present experiments, electroporation produced the highest fraction of single gene incorporations. Sequence analysis indicated that approximately 75-80% of the colonies carries only a single library member.

Example 5

Library Screening

After digestion with SacI and ethanol precipitation, the pPIC9-cp-calB library was transformed into electro-competent *P. pastoris* strain GS115 (as described in Wu, S. et al., *Biotechniques* 2004, 36, (1), 152-4, which is hereby incorporated by reference) and plated on MM-tributyrin plates. Upon expressing a lipase variant, the yeast exports the pro-protein into the cell's surrounding media as defined by the attached α-signal sequence. Following cleavage of the lipase's pro-sequence by an extracellular protease, functional library members will hydrolyze the emulsified tributyrin, a short-chain triglycerate, into water soluble products which creates a "clearing zone," as illustrated in FIG. 4, around that particular colony. Tributyrin is considered an easy substrate that can be utilized by the vast majority of known lipases.

Colonies appeared after four days of incubation at 30° C. Active cp-CALBs were identified by the formation of a clear halo surrounding the respective host colony, as described in Gupta, R., et al., *Biotechnol Appl Biochem* 2003, 37, which is hereby incorporated by reference. The growth of the cp-library on these screening plates produced several hundred halo-forming colonies. These colonies were picked and replated on MD and MM-trybutyrin plates to verify the lipase activity in a secondary screening, also illustrated in FIG. 4. After confirmation of the lipase activity, the sequences of the corresponding cp-CALB genes were obtained by colony PCR and DNA sequencing using primers ZQ-pPIC9-for (5'-TAC-TATTGCCAG CATTGCTGC-3') (SEQ. ID NO: 12) and ZQ-pPIC9-rev (5'-GCAAAT GGCATT CTGACATCC-3') (SEQ. ID NO: 13).

Figure 5:
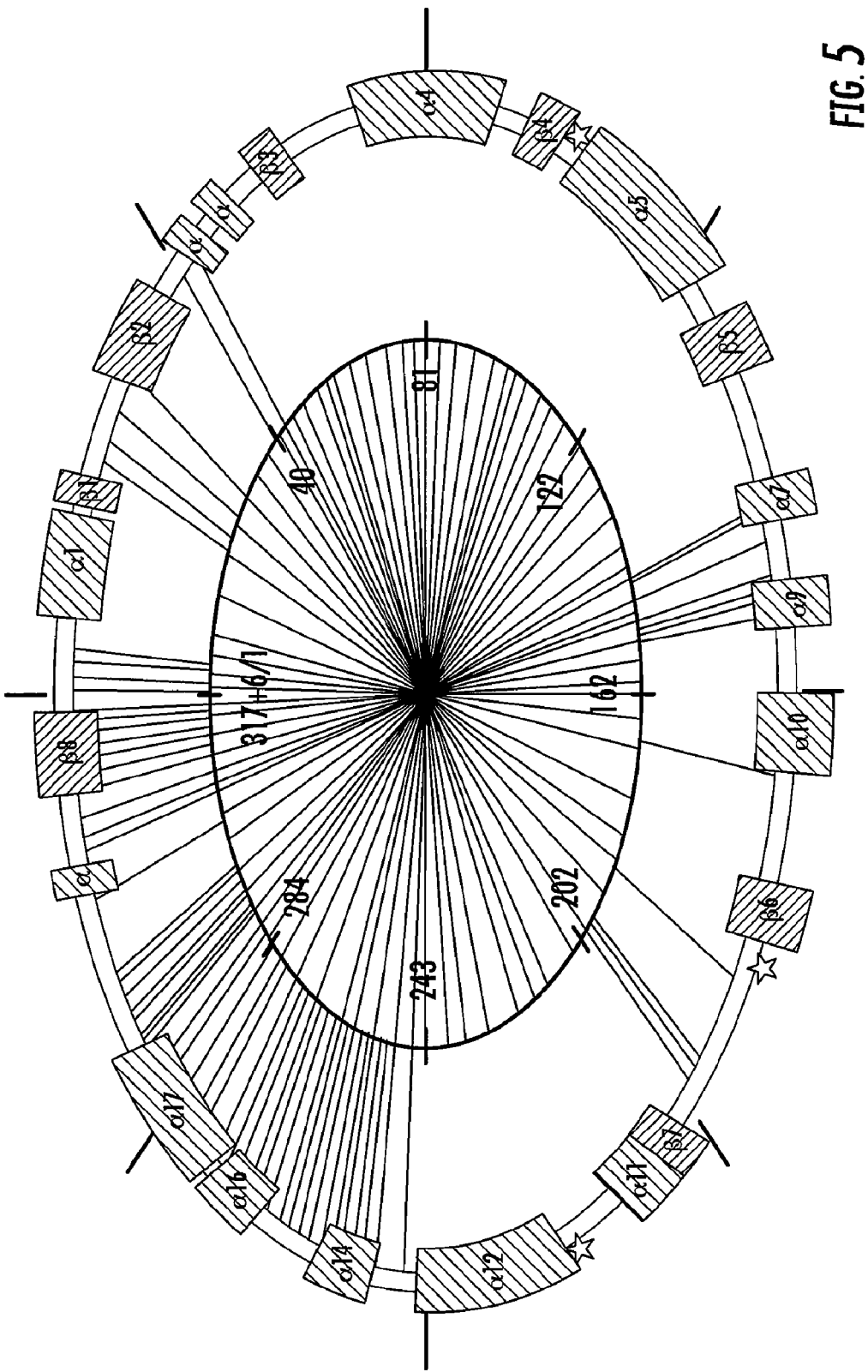
FIG. 5 is a circular permutation diagram of CALB illustrating the distribution of the termini location of 63 functional library members with unique sequences (outer circle).

Sequence analysis of 280 colonies led to the identification of 63 unique circular permutated CALBs, and the distribution of the selected variants was visualized in FIG. 5 (outer circle lines). As the growth temperature of the culture could potentially bias the outcome of the screening experiment by favoring proteins with higher thermostability, these experiments were conducted at room temperature, as well as 30° C. No differences in the distribution were however detected. Furthermore, the impact of the N-terminal His-tag on lipase variant screening and function was investigated. Protein libraries without the His-tag showed the same distribution of functional permutants as the tagged variants.

The analysis of the current 63 functional lipase variants, and mapping of the new termini location on the tertiary structure of CALB (FIG. 6) gives raise to some interesting results. While a good number of permutations are located in surface loop regions as expected, FIG. 6 indicates that the C-terminal region appears to be more susceptible to the introduction of backbone cleavage without loss in function. In particular, the bent helix 16-17 of the cap domain can be cleaved at almost every single amino acid. This result is even more exciting as the hinge region between the two helices covers a significant portion of CALB's active site. The introduction of a backbone cleavage is therefore likely to affect the catalytic performance of the enzyme. A second region with multiple permutations is the region of helix 7-9 that constitutes the lid region of CALB. Although smaller and less important for the function of CALB, this region is important for most lipases as it undergoes an important conformational change that activates the lipase. Surprisingly, permutations were also found in helix 2 that forms part of the oxyanion-binding pocket in the active site. All indicated permutation sites were confirmed by isolation of the corresponding gene, retransformation, verification of the halo formation, and repeated DNA sequencing.

Example 6

Protein Expression and Purification

The overexpression and purification of wild type CALB was performed as described in Rotticci-Mulder, J. C. et al., *Protein Expr Purif* 2001, 21, (3), 386-92, which is hereby incorporated by reference. The same protocol was adopted for the isolation of circular permutation variants of CALB. Briefly, pPIC9-ca/B was linearized by SacI digestion and electroporated into *P. pastoris* cells (GS115). Aliquots were plated on MD His⁻ plates and incubated at 30° C. Colonies appeared on plates after 2 days of incubation. A single colony was picked to inoculate 25 ml BMGY medium and the culture was incubated at 30° C. until it reached an $OD_{600}$ of 2-6. The cells were harvested and resuspended in BMMY medium to an $OD_{600}$ of 1. Protein expression was induced by addition of methanol to a final concentration of 0.5% (v/v) every 24 hours. After 4 days of incubation, the culture medium containing the lipase was separated from the cells by centrifugation (1500 g, 4° C., 10 min).

The His-tagged CALB was isolated from the clear supernatant via affinity chromatography on Ni-NTA agarose (Qiagen, Valencia, Calif.) using 2.5 ml resin per 100 ml supernatant. The column was washed with two column volumes of buffer 1 (20 mM imidazole, 300 mM NaCl, 50 mM $NaH_2PO_4$, pH 8.0) and enzyme was eluted in two column volumes of buffer 2 (250 mM imidazole, 300 mM NaCl, 50 mM $NaH_2PO_4$, pH 8.0). All fractions were analyzed by SDS- PAGE and product-containing aliquots were pooled. Purified CALB was exchanged into storage buffer (150 mM NaCl, 50 mM K-phosphate, pH 7.0) by ultrafiltration (Amicon Ultra-4 centrifugal filter unit; Millipore, Bedford, Mass.), and stored at 4° C. The protein concentration was determined spectrophotometrically at 280 nm ($\epsilon=3.3\times10^4$ $M^{-1}$ $cm^{-1}$), as described in Rotticci, D. et al., *Biochim Biophys Acta* 2000, 1483, (1), 132-40, which is hereby incorporated by reference.

Alternatively, hydrophobic interaction chromatography (HIC) in combination with size exclusion chromatography was employed to purify CALB to homogeneity as described above. The two-step purification enables the rapid isolation of lipase variants whose His tag is not accessible (circular permutants with termini in the protein's interior region) or has been removed all together. Addressing concerns that the His-tag may interfer with the enzyme function, a second selection of experiments we performed with same calB library without affinity tag. The DNA sequence analysis of functional candidates indicated that the location and distribution of permutation sites in functional CALB variants was the same as shown in FIG. 5. For the HIC purification route, the clear culture supernatant was mixed with 2 M $(NH_4)_2SO_4$ solution and 1 M K-phosphate buffer (pH 7.0) to a final concentration of 1 M and 50 mM respectively. The protein samples were then loaded on a HIC column (7 ml butyl-sepharose 4 resin (AmershamBiosciences, Piscataway, N.J.), pre-equilibrated with 1 M $(NH_4)_2SO_4$, 50 mM K-phosphate buffer (pH 7.0) (buffer 4). The column was rinsed with 4 volumes of buffer 4, followed by a stepwise reduction of $(NH_4)_2SO_4$ in the phosphate buffer (0.2 M increments, 4 column volumes per step). Lipase activity in the eluant was monitored via p-NB hydrolysis (see below) and fractions containing the desired activity were pooled and concentrated by ultrafiltration (Amicon Ultra-15 centrifugal filter unit; Millipore, Bedford, Mass.). According to SDS-PAGE, the eluted protein has >85% purity. Further removal of contaminants was possible by gel filtration on a Superdex-200 10/300 GL column (AmershamBiosciences, Piscataway, N.J.), using 50 mM K-phosphate buffer (pH 7.0) containing 150 mM NaCl. SDS-PAGE analysis of the final product showed >95% purity.

Example 7

Activity Assays

Lipase activity was determined by measuring the initial hydrolysis rate of p-NB and DiFMU octanoate at room temperature on a Synergy-HT microtiterplate reader (Bio-Tek Instruments, Winooski, Vt.). Stock solutions of p-NB (200 mM) and DiFMU octanoate (3 mM) were prepared in DMSO. p-NB hydrolysis over a substrate range of 0-1.6 mM was measured in 50 mM K-phosphate buffer (pH 7.5) at 400 nm ($\epsilon$ for p-NB=13260 $M^1$ $cm^{-1}$) as described in Bender, M. L. et al., *J Am Chem Soc* 1968, 90, (1), 201-7, which is hereby incorporated by reference. The rate of DiFMU octanoate hydrolysis was determined by measuring the DiFMU formation over a substrate range of 0-12 μM in 50 mM K-phosphate buffer (pH 7.0) at an excitation/emission wavelength 360/460 nm. Kinetic constants were calculated by fitting the initial rates to the Michaelis-Menten equation using the Origin® software (version 7; OriginLab Corporation). The results are presented in Tables 1 and 2, above.

Example 8

Large-scale Lipase Overexpression for Biochemical & Biophysical Studies

A batch-fermentation protocol for overexpressing CALB in *Pichia pastoris* was established and implemented. The experiments with wild type and permutated CALBs consistently yield ~600 mg protein per liter of culture medium. The target protein is secreted into the culture medium and can be isolated with >95% purity via one-step purification over a weak ion-exchange resin.

For experiments in organic solvents, CALB is immobilized on Lewatit VPOC 1600 (Sybron Chem. Inc) and the amount of active lipase on the resin is quantified via active site titration with the suicide inhibitors (as described in Rotticci D., et al., An active-site titration method for lipases. *Biochim Biophys Acta* 2000, 1483:132-140; and Fujii R, Utsunomiya Y, Hiratake J, Sogabe A, Sakata K: Highly sensitive active-site titration of lipase in microscale culture media using fluorescent organophosphorus ester. *BBA-Molecular and Cell Biology of Lipids* 2003, 1631:197-205. Such a suicide inhibitor, methoxy-4-methylumbelliferyl hexylphosphonate, has been synthesized and successfully used to determine enzyme loads on the resin.

Example 9

Kinetic Analysis of Lipase Catalyzed Transesterification Reactions

Transesterification of 6-methyl-5-hepten-2-ol with vinyl acetate was performed in hexane at 23° C. Each 1 ml reaction mixture contains from 1-10 mg immobilized enzyme, 50 mM internal standard 6-methyl-5-hepten-2-one and varying amount of racemic 6-methyl-5-hepten-2-ol (25~500 mM). The mixture was incubated at 23° C. for 30 minutes and the reaction was initiated by the addition of 0.5 mmol vinyl acetate. Samples at different time points were taken to determine the initial reaction rates. For each reaction at least five samples were taken, and the overall conversions was limited to 5% of the substrate. The samples were analyzed by gas chromatography G6850 (Agilent Technologies) installed with a Cyclosil-B column (length 30 m, i.d. 0.32 mm, film 0.25 mm, Agilent) connected to a flame ionization detector. Hydrogen was used as the carrier gas, and the temperature program was: 70° C. for 1 min, 2° C./min to 90° C. and hold for 3 min, then 10° C./min to 120° C. and hold for 3 min. The retention time was 12.2 min for S-6-methyl-5-hepten-2-ol and 12.8 min for its R-enantiomer.

Transesterification of 3-hydroxy tetrahydrofuran with vinyl acetate was performed the same except that acetonitrile was used as solvent. The temperature program for GC analysis was: 65° C. for 5 min, 2° C./min to 90° C., then 10° C./min to 120° C.

Example 10

Incremental Truncation of C-terminus of Wild Type CALB

Wild type CALB gene (SEQ ID NO: 1) was PCR amplified using primers CALB_for_hisfree (5'-CGCCTCGAG AAAAGAGAGGCTGAAGCTCTACCTTCCGGTTCGG-ACCCTGCC-3') (SEQ ID NO: 24) and ZQ_CALB_rev (5'-CGCGCGGCCGCTTAGGGGGTGACGATGCCGGAG-CA-3') (SEQ ID NO: 7). The PCR product was digested with NotI and XhoI and ligated into the vector pAMB-CAT digested with the same restriction enzymes. The plasmid was linearized by EcoRI digestion, and the incremental truncation library was generated following the protocol of Marc Ostermeier and Stefan Lutz (Methods in molecular biology, Vol 231, 129-142). In detail, the linearized plasmid was amplified by Taq DNA polymerase using primers Trunc_for (5'-

GAGCTCCGTCGACAAGCTTGCGG-3') (SEQ ID NO: 28) and Trunc_rev (5'-GGATGAGCATTCATCAGGCGGGCA-3') (SEQ ID NO: 29). The 50 µl PCR reaction mixture contained 175 µM dNTP/25 µM αS-dNTP (dNTP:αS-dNTP=7:1). After purification with Qiagen's QIAquick PCR purification kit, the PCR product was digested by Exonuclease W (120 units/µg DNA) at 37° C. for 30 min. The reaction was quenched by the addition of 5 volumes of PB buffer and purified by QIAquick PCR purification kit. The 5'-overhang was removed by incubation with mung bean nuclease (2.5 units/µg DNA, DNA concentration 0.1 µg/µl) at 30° C. for 30 min, and the DNA was purified by Qiagen spin columns. Then the purified DNA was treated with Klenow polymerase to repair the sticky ends (1 units/µg DNA, DNA concentration 0.1 µg/µl, 25° C. for 15 min and 75° C. for 20 min). After purification by Qiagen spin column, the DNA was digested with XhoI, and size selection (fraction between 750 bp and 1 kb) was performed afterwards by gel extraction.

The extracted DNA was ligated into a modified vector pAMB-pET digested with PsiI and XhoI, and transformed into *E. coli* DH5α cells. Around $1.5 \times 10^5$ colonies were obtained. The cells were harvested and the plasmid was purified by Qiagen miniprep kit. After digestion the plasmid with NotI and XhoI, the fraction containing CALB gene fragments was extracted and ligated into the plasmid pPIC9 digested with the same enzymes. The ligation mixture was again transformed into DH5α, and a library of 1.2 million colonies was obtained. The plasmid was purified, digested with SacI, transformed into *Pichia Pastoris* strain GS115 and plated on MM-tributyrin plates. Active library members were visualized by halos around the colonies. Those colonies were picked and submitted to DNA sequencing.

TABLE 3

Activity of truncation members

| CALB Truncation Peptide | Activity (Y/N) |
|---|---|
| Δ296 | N |
| Δ288 | N |
| Δ277 | N |
| Δ254 | N |
| Δ249 | N |
| Δ301 | Y |
| Δ302 | Y |
| Δ303 | Y |
| Δ304 | Y |
| Δ305 | Y |
| Δ306 | Y |
| Δ307 | Y |
| Δ308 | Y |
| Δ309 | Y |
| Δ310 | Y |
| Δ312 | Y |
| Δ313 | Y |
| Δ314 | Y |

Example 11

Incremental Truncation of the External Loop of cp283

In the present example, incremental truncation of the extended loop of CALB-cp283 was performed to evaluate the effect on the thermostability of the variants. The gene encoding the peptide sequence of cp283 (SEQ ID NO: 14) was put into the vector pAMB-CAT using NotI and XhoI restriction sites. Then the plasmid containing cp283 gene was linearized by SpeI digestion (which is within the six amino acid linker between natural C- and N-termini). The linearized plasmid was amplified by Taq DNA polymerase using primers ZQ_cpCALB_for (5'-GGTA CTAGTGGTGGCCTACCT-TCCGGTTCGGACCCT-3') (SEQ. ID NO: 8), ZQ_cpCAL-Brev (5'-CGCACTAGTACCGCCGGGGGTGACGAT-GCGGG AGCA-3') (SEQ ID NO: 9), and spiked dNTPs (dNTP:αS-dNTP=7:1). The incremental truncation library was generated the same way as the C-terminal truncation library, except that intramolecular ligation was performed after the Klenow polymerase treatment (DNA concentration: 2.5 ng/µl, 16° C. overnight). The ligation mixture was concentrated by ethanol precipitation and electroporated into DH5α. About 3 million colonies were obtained. Purified plasmid was subjected to NotI and XhoI digestion, and the DNA fragment between 750 and 1000 bp was extracted from agarose gel. The fragment was ligated into the vector pPIC9, and the following procedure was the same as the C-terminal truncation library. Partial sequences, showing the location of deleted segments, of some the members of the cp283 truncation library are illustrated in FIG. 9.

Functional variants were identified by screening for tributyrin hydrolysis. It was found that up to 11 amino acids (approximately 25% of the extended loop) could be deleted without the loss of function. All variants up to cp283Δ11 retain the p-nitrophenol butyrate hydrolysis activity of CALB cp283 (data not shown). The linker region and wild type C-terminal region were found to be more tolerant to truncation than the wild-type N-terminal region. As shown in FIG. 11, variants cp283Δ2 to Δ7 demonstrated increasing $T_M$ and wild type-like secondary structure content, while cp283Δ8 to Δ11 showed lower $T_M$ and loss of secondary structure content. This abrupt transition at Δ7/Δ8 may reflect critical loop size for proper orientation of the cp283 N-terminus.

Gel filtration analysis was perfomed to assess the quaternary structure and aggregation of truncated cpCALB variants, to determine whether over-truncation of the loop and removal of disulfide-forming Cys295 could affect stability and lead to aggregation. As illustrated in FIG. 10, this analysis revealed that loop truncation in the variants affected the dimerization ability of the peptide. The dimeric form of CALBs was found to be stable and can be isolated for additional characterization. Analysis of cp283Δ4 monomer and dimer forms demonstrated that both protein forms have high catalytic activity, but the enhanced thermostability appears to be due to dimerization. It is believed that truncation of the extended loop allows proper adjustment of loop length to optimize dimerization by domain swapping of N-terminus in cp283Δ7.

The results of the present study suggest that amino acid deletions in the extended loop of the CALB linker region results in more native-like secondary structure and increased stability. Furthermore, it appears that the increase in stability is not necessarily due to lower entropy of loop closure, but may be attributed to the increased ability to dimerize in variants with optimal loop size and configuration.

It should be emphasized that the above-described embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

Example 12

Circular Permutation Effects on Enantioselectivity and Structure

Random circular permutation generates small variations in polypeptide chain length, resulting from the insertion and deletion of amino acids at the new termini. While some of the example above show that neither modification of the protein sequence seems to affect function per se, potential effects on stability and overall catalytic efficiency could not be ruled out. Therefore, in the present study, the gene sequences of all previously characterized CALB variants were corrected, making them uniform in size with wild type protein by removing amino acid duplications and filling in missing residues with gene-specific primers. All variants used in this study were 323 amino acids in length, 317 residues from the native enzyme plus 6 amino acids from the linker sequence. Furthermore, the N-terminal His-tag was removed to eliminate the potential for interference with catalysis. The tag was initially used for protein purification, yet changes in the experimental protocol have made its presence optional.

The present study included ten CALB variants. Six variants had new termini in the cap region, the lid permutants cp144, cp148, and cp150, as well as the helix 16/17 permutants cp283, cp284, and cp289. This set of enzymes was complemented with three additional helix 16/17 variants (cp268, cp277, cp278). The combination of these ten enzymes represents a set of biocatalysts with permutation sites along the entire length of the two surface-exposed helices. Furthermore, cp193 was included in this study, a variant with its termini near Asp187 of the catalytic triad, to assess the effects of backbone cleavage near residues of the catalytic triad.

Kinetic Characterization with Reference Substrates

Given the size adjustments to the previously characterized CALB variants plus the addition of new enzymes for this study, all ten enzymes were characterized with reference substrates p-nitrophenol butyrate (p-NB) and 6,8-difluoro-4-methylumbelliferyl (DiFMU) octanoate (see Tables 1 and 2, in the detailed description above). The kinetic properties of cp144, cp148, and cp150 remained unchanged from previous examples. Similarly, cp283-289 show little deviation from previous data for p-NB hydrolysis. In contrast, the removal of the termini extensions in cp283 and cp284 resulted in an additional ten-fold improvement in DiFMU octanoate turnover (see cp283a and cp284a in Tables 1 and 2 in the detailed description above), raising the catalytic efficiency of these two variants over wild type CALB by 175 and 141-fold respectively. In both cases, the higher specificity can be attributed exclusively to higher rate constants as the KM values are the same as wild type. It is believed that these gains in activity could be linked to reduced steric interference in the active site binding pocket or reflect changes in the conformational flexibility of these regions. Interestingly, cp289 with its termini shifted by 5 amino acids to a position outside helix 17 shows no significant change in catalytic performance, maintaining high activity for DiFMU octanoate with or without termini extensions.

Enantioselectivity of Circular Permuted CALB

Significant rate enhancements in engineered enzymes are frequently reported, yet often come at the expense of a catalyst's enantioselectivity. Furthermore, the reactivity of the leaving groups in these two reference substrates has raised questions as to the enzymes' performance with regular, unactivated substrates. To address both concerns, a second series of kinetic experiments were conducted, comparing the esterification and transesterification of five chiral alcohols and carboxylates with wild type CALB and cp283, the lipase with the highest rate acceleration in the previous tests.

Milligram quantities of both enzymes could be obtained by scaling up protein overexpression in *Pichia pastoris* and immobilizing the secreted lipase on weak ion-exchange resin as described in the experimental section. The immobilized enzyme was quantified by active site titration assay using the suicide inhibitor methyl 4-methylumbelliferyl hexylphosphonate. Upon reacting in the lipase active site, the inhibitor releases a stoichiometric amount of highly fluorescent 4methylumbelliferone (4-MU), which can be used to calculate the enzyme load on the resin. The immobilized enzymes were used to catalyze the described esterification and transesterification reactions in organic solvents.

Based on wild type CALB's substrate preference and high enantioselectivity for secondary alcohols, three racemic secondary alcohols with substituents of various size were chosen as test substrates.

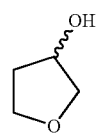

R/S-1

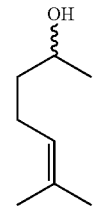

R/S-2

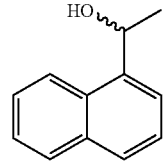

R/S-3

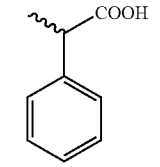

R/S-4

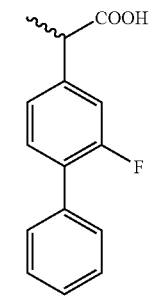

R/S-5

The kinetic constants for the transesterification reaction of 3-hydroxy-tetrahydrofuran (1), 6-methyl-5-hepten-2-ol (2), and 1-(−1-naphthyl)ethanol (3) with vinyl acetate were measured (FIG. 12, Table 2). The results indicate that circular permutation does not affect the enantiomeric preference of CALB. Both wild type enzyme and cp283 strongly favor the (R)-isomers of 2 and 3. The GC analysis of the reaction mixture containing the (S)enantiomer showed no detectable product formation over the length of the assay. The reported minimum enantiomeric ratio (E-values) for these two substrates were estimated based on the instrument's detection limit. In the case of 1, the two enzymes switched to (S)-isomer preference but did not show superior enantioselectivity. The result can be explained by the symmetry of the substrate's oxolane ring which makes it difficult for CALB and other lipases, which rely on size differences of the two substituents on the alcohol moiety, to distinguish the two stereoisomers. For all three substrates, the calculated E-values for the permuted enzyme were similar to wild type CALB, confirming that the enantioselectivity of the lipase was not compromised as a result of circular permutation. Equally important, the kinetic data for cp283 showed little deviation from the wild type enzyme. For 1, a two-fold higher KM but similar turnover rate resulted in a slightly lower performance constant for cp283 than wild type CALB. In contrast, the engineered variant and wild type enzyme had virtually identical Michaelis-Menten binding constants for 2 and 3. Similar to the results with the two reference substrates, cp283 showed noticeably higher turnover rates for 2 and 3, raising kcat/KM by up to three-fold.

Separately, the CALB-catalyzed esterification of two chiral carboxylates, 2-phenyl propionic acid (4) and 2-(3-fluoro-4-phenyl-phenyl)propionic acid (flurbiprofen, 5), with n-propanol was studied (FIG. 12, Table 2). Consistent with the results for the chiral secondary alcohols, both enzymes favor the (R)-enantiomers of 4 and 5. Although both stereoisomers are turned over, a combination of elevated KM and lower kcat values results in the discrimination against the unfavorable (S)-isomer in both enzymes. Furthermore, changes in the individual performance constants lead to overall two-fold improved E-values for cp283. Finally, the comparison of the kcat/KM values for the two enzymes with the respective substrates showed a 2 to 4-fold higher performance constant for the engineered enzyme over wild type CALB. While the catalytic activity and enantioselectivity of cp283 is improved, the underlying cause for the performance enhancement might differ for the two substrates. The catalytic gains for 4 seem to originate largely from a lower KM value for the (R)-isomer, while the higher kcat/KM for 5 results from an increase in catalytic activity for the preferred enantiomer.

In summary, the results from these kinetic experiments demonstrate that circular permutation of CALB does not compromise the enantioselectivity of the biocatalyst. To the contrary, improvements in enantioselectivity plus elevated catalytic efficiency were observed for a number of tested substrates. As such, the experiments confirm the above results that circular permutation in selected portions of CALB can raise the enzyme's catalytic activity for a substrate. Cp283's consistently higher turnover rate and improved enantioselectivity, even for unactivated substrates, demonstrates the potential of CP in improving an existing biocatalyst.

Structural Consequences of Circular Permutation

In parallel with the kinetic analysis of the above CALB variants, the impact of circular permutation on protein structure were also explored. Cp193 was excluded from these studies due to protein instability. In initial experiments, the effects of termini relocation on the tertiary structure of CALB were assessed by intrinsic tryptophan fluorescence, using its seven native indole side chains for detecting changes in tertiary structure. In addition, this study looked for changes in protein folding and packing with 1-anilino-8naphthalene sulfonate (ANS), an environmentally sensitive hydrophobic fluorescence dye. Both analyses showed no significant spectral deviation from wild type CALB, consistent with overall compact, native-like tertiary structures for all the variants (data not shown). These findings reaffirm that CP generally has little impacts on the overall protein tertiary structure. Instead structural changes usually are concentrated in two regions, the native and the newly created termini.

Figure 7:
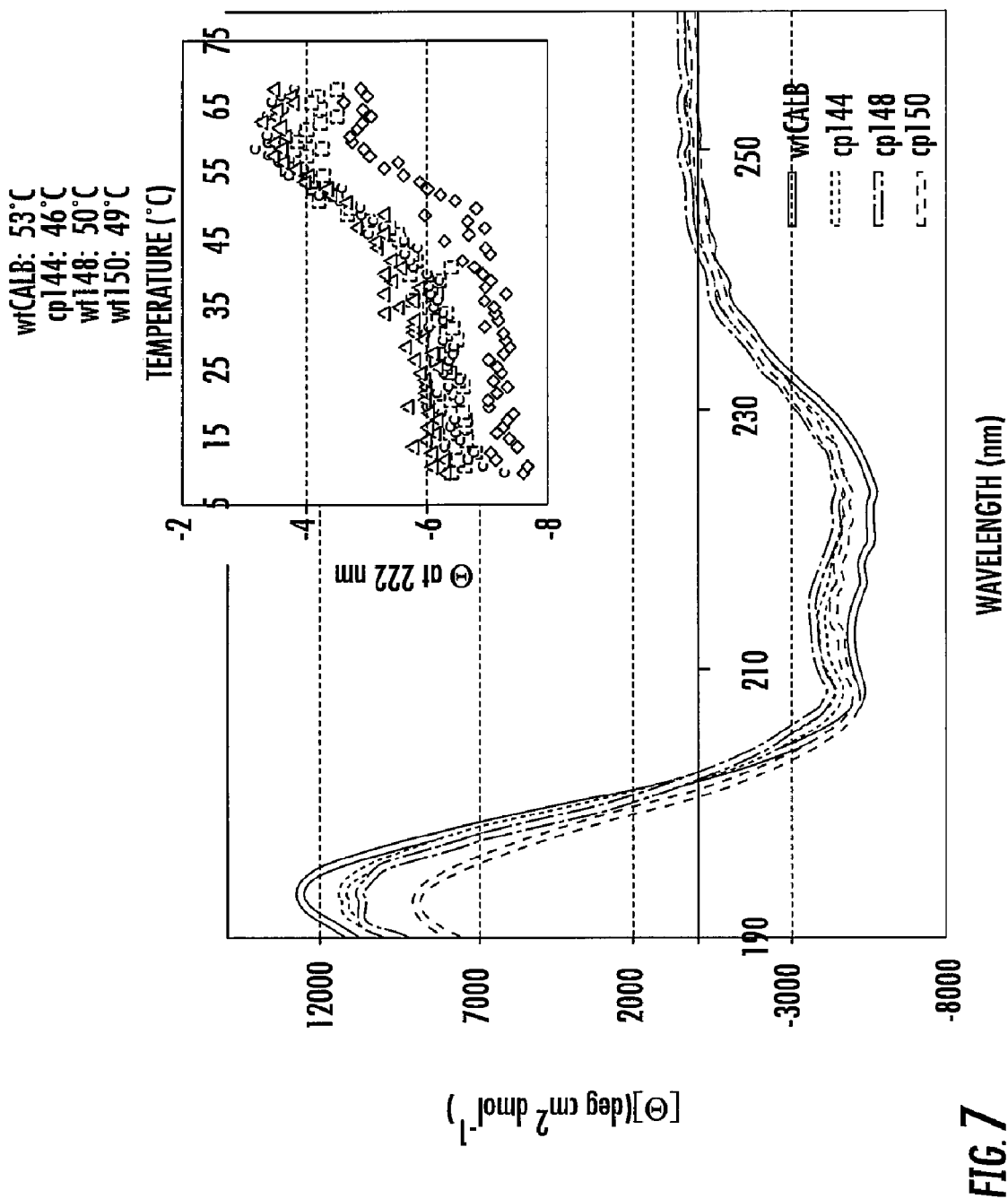
FIG. 7 is a far-UV circular dichroism spectra for CALB variants with new termini in helix 7/9. The insert is a graph of thermostability data for the same variants.
Figure 8:
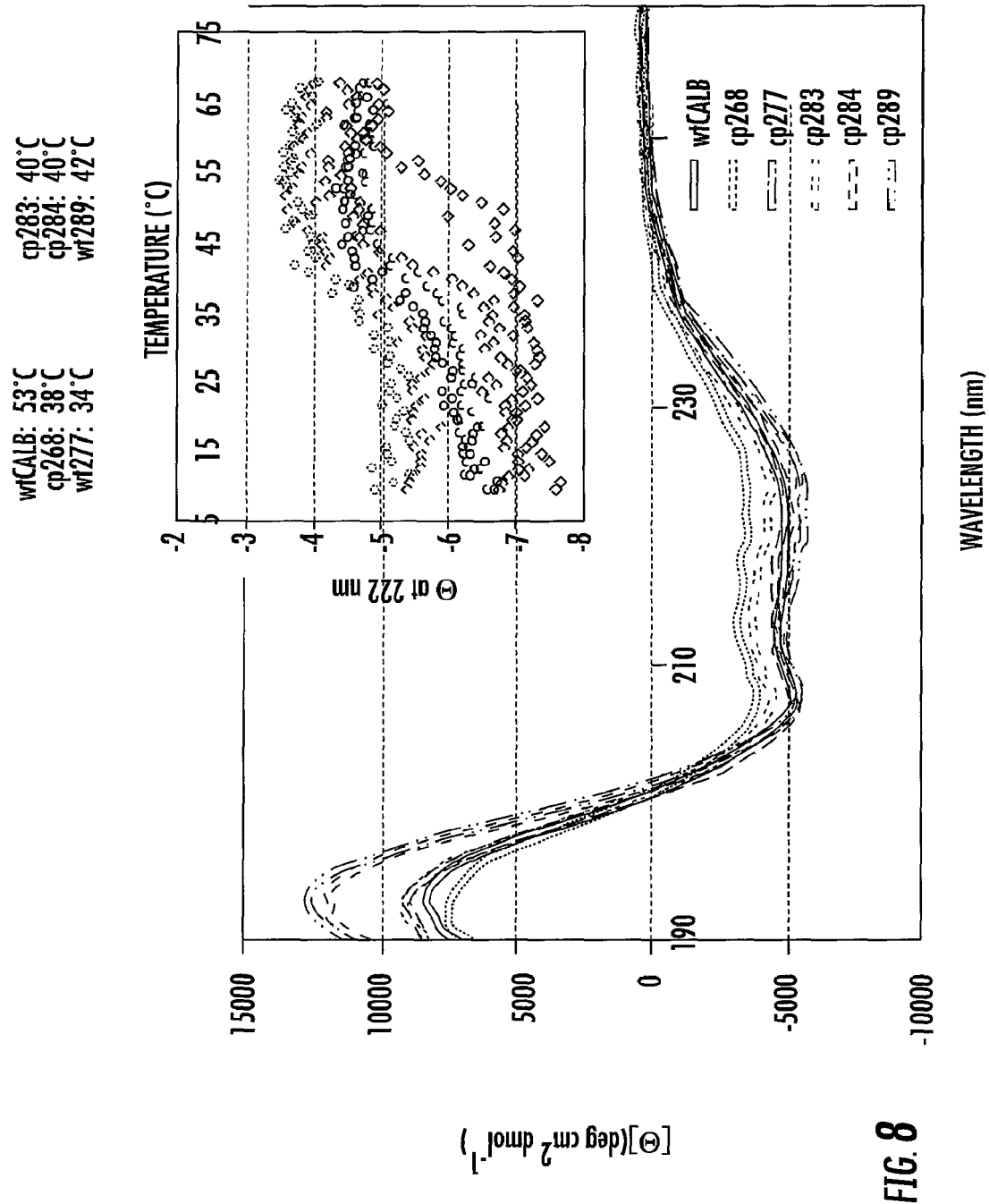
FIG. 8 is a far-UV circular dichroism spectra for CALB variants with new termini in helix 16/17. The insert is a graph of thermostability data for the same variants

Circular dichroism (CD) spectroscopy in the far UV range revealed significant changes in the secondary structure content of circular permuted CALB variants (FIGS. 7 and 8, discussed above). All permuted proteins maintained a mixed α-helix/β-sheet spectral signature, yet their mean residue ellipticity (Θ) at 193 nm was consistently lower and the minima at 209 nm and 222 nm lost intensity compared to wild type enzyme. These observations are consistent with a decline in helical content. The data interpretation was confirmed in secondary structure models of the MRE curves by DICHROWEB (FIG. 13, Table 3). Accompanying the observed decline in helical content, thermo-denaturation studies of these variants in the CD spectropolarimeter also showed a significant drop in the temperature of unfolding from 53° C. for wild type CALB to, in the worst case, 34° C. for cp277 (FIG. 13, Table 3). Permutations in the lid region (cp144-cp150) appear less destabilizing, causing difference in TM values of only 3 to 7° C., while TM values for CALB variants with new termini in helix 16/17 (cp268-cp289) fell by 12 to 19° C., depending on the termini location.

More interestingly, the TM values show a correlation with the far UV CD results and kinetic data for the reference substrates. This data set indicates that placing α16/17 at the protein's C-terminus, as is the case for cp289, seems less detrimental to structure and function than positioning the helix at its N-terminus as in cp268. It is believed that in cp289, the glycine-rich linker, connecting the native termini, creates an extended, structurally poorly-defined region at the new N-terminus whose proper organization in the enzyme tertiary structure is not critical for catalytic function. Such an interpretation is supported by incremental truncation experiments, discussed above, showing that wild type CALB tolerates deletion of up to 16 amino acids at its native C-terminus without loss of function. *Helix* 16/17 in cp289 forms the new C-terminus and, as suggested by the enzyme's native-like CD signature, can assume a defined secondary structure. In contrast, cp268 represents the other extreme where helix 16/17 is positioned at the N-terminus, connected to the rest of the protein via the extended linker. It is believed that the higher flexibility of this linker region complicates the proper orientation of the helix in this CALB variant, negatively affecting not only overall protein stability and helix formation, but consequently also catalytic function.

In separate experiments, the idea of substrate-induced conformational changes was tested. Speculating that the presence of a substrate in the active site could stabilize the termini regions and lead to greater structural organization, the spectroscopic properties of wild type CALB and cp283 were measured after derivatization with the suicide inhibitor methyl 4-methylumbelliferyl hexylphosphonate. The presence of the bound inhibitor substantially raised the TM for both enzymes to 68 and 63° C. respectively, yet left the far-UV CD signatures unchanged (data not shown). These results suggest the absence of direct interactions between the substrate and the new termini region. Not unexpected, enzyme immobilization also increases the stability of these CALB variants. The esterification experiments of 4 and 5 were carried out at 50° C. without noticeable reduction in enzyme activity after more than an hour at elevated temperature.

Discussion

Circular permutation of CALB can generate engineered enzymes with over 100-fold enhanced performance constants without compromising the biocatalyst's enantioselectivity. These observations demonstrate that CP does not dismantle the active site but seems to introduce more subtle conformational changes that benefit catalysis when the termini are located in proximity to the active site. In contrast, backbone cleavage that affects the proper geometry of the catalytic triad will be detrimental to function as seen for cp193 and cp44/cp47. Furthermore, the fluorescence and CD spectroscopy data support the original hypothesis that the termini relocation impacts mostly local protein structure near the old and new termini.

Focusing on the old and new termini regions in the most active CALB variants with termini in the helix 16/17 region, a correlation between catalytic activity, stability and position of the backbone cleavage site was noted. Fragments of helix 16/17 on the N-terminal portion of the CALB variants appear to lack stability due to the adjacent extended loop structure consisting of the native termini and the flexible six-amino acid linker. Such extended loops in proteins have been shown to be destabilizing to the protein overall and could explain the reduction on the TM values of these variants, as explored in more detail in Example 11, above.

Materials and Methods

Chemicals: Fluorogenic substrate 6,8-difluoro-4-methylumbelliferyl octanoate (DiFMU octanoate) and the reference standard 6,8-difluoro-7-hydroxy-4-methylcoumarin (DiFMU) were purchased from Molecular Probes (Eugene, Oreg.). p-Nitrophenyl butyrate (p-NB), 6-methyl-5-hepten-2-ol, 3hydroxytetrahydrofuran, 1-(1-naphthyl)ethanol, flurbiprofen, and phenylpropionic acid were purchased from Sigma (St. Louis, Mo.). Enzymes were purchased from New England Biolabs (Beverly, Mass.) unless noted otherwise.

Strains and media: $E.\ coli$ strain DH5α-E (Invitrogen, Carlsbad, Calif.) was used for all vector construction. Bacteria were grown under standard conditions in Luria-Bertani (LB) liquid media or on LB agar plates supplemented with the appropriate antibiotics. Lipases were overexpressed in $Pichia\ pastoris$ GS115 (his4) (Invitrogen, Carlsbad, Calif.). $P.\ pastoris$ was cultured in YPG medium (10 g yeast extract, 20 g bacto peptone, 20 g glucose per liter). For protein overexpression, we used BMGY medium (10 g yeast extract, 20 g peptone, 13.4 g yeast nitrogen base, 0.4 mg biotin, 10 ml glycerol, and 100 ml 1 M potassium phosphate buffer, pH 6.0 per liter) and BMMY medium (10 g yeast extract, 20 g peptone, 13.4 g yeast nitrogen base, 0.4 mg biotin, 5 ml methanol, and 100 ml 1 M potassium phosphate buffer, pH 6.0 per liter).

Construction of vectors: To express CALB variants with defined termini, the genes of selected lipases in the random circular permutation library were PCR amplified with the corresponding primers. The PCR products were digested with XhoI and NotI and ligated to the vector pPIC9 (Invitrogen, Carlsbad, Calif.) digested with the same restriction enzymes. Following transformation into $E.\ coli$ DH5α-E, plasmids were isolated and the correct calb sequences confirmed by DNA sequencing. Protein expression, purification & standard activity assays: The laboratory-scale overexpression and purification of wild type CALB and the variants was performed as previously described in the Examples above. Spectrophotometric assays to measure lipase activity with the reference substrates p-NB and DiFMU octanoate were performed as described. All experiments were performed in triplicate. Kinetic constants were calculated by fitting the initial rates to the Michaelis-Menten equation using Origin7 (OriginLab, Northhampton, Mass.).

CD analysis: Far-UV circular dichroism (CD) spectra were obtained using a J-810 spectropolarimeter (Jasco, Easton, Md.). Spectra were recorded at 10° C. from 260-190 nm (0.5 nm increments) using a 0.1 mm pathlength cell, 20 nm/min scan rate, 4 s response time, and 2 nm bandwidth. Proteins were analyzed at concentrations of 1 mg/ml (as determined by UV absorbance at 280 nm; $\epsilon$=33000 $M^{-1}\ cm^{-1}$) in potassium phosphate buffer (50 mM, pH 7). Recorded data represent the means of five scans. Spectra were corrected for buffer absorbance and converted to mean residue ellipticity ([θ] mrw). Thermal denaturation was monitored by following the ellipticity at 222 nm at a 1° C./min heating rate from 10 to 80° C.

$P.\ pastoris$ fermentation: Fermentation was performed in a 5-liter New Brunswick BioFlow 3000 fermenter (New Brunswick Scientific, Edison, N.J.). The reaction conditions and media composition were chosen based on Invitrogen's standard protocol for $Pichia\ pastoris$ fermentation. Briefly, the glass fermentation vessel containing half the working volume of fermentation basal salts medium was sterilized. Following sterilization, the pH of the medium was adjusted to 5.0 and PTM1 trace salts were added. Fermentation conditions for Mut+GS115 transformants were set as following: 30° C., 500 rpm agitation, DO 30%, pH 5. The reactor was inoculated with 10% of the initial fermentation volume. Upon reaching a cell wet-weight of 180 g/L, the culture was induced with methanol for 2 days. Cells were harvested and the supernatant was collected and filtered using Millipore 0.22 μm filter.

Protein Immobilization: Ion exchange resin Lewatit VP OC 1600 (Lanxess, Pittsburgh, Pa.) was used for lipase immobilization. Resin was pre-washed with ethanol and dried under vacuum. For immobilization, 1 g resin was repeatedly incubated with 50 ml aliquots of filtered fermentation supernatant in a head-over-head shaker at 4° C. Upon reaching saturation of the resin as detected by increasing enzyme activity in the supernatant, the resin was washed with 50 mM potassium phosphate buffer (50 mM, pH 6.0), dried under vacuum and stored at 4° C.

Synthesis of Methyl 4-methylumbelliferyl hexylphosphonate: The synthesis was performed as described in R. Fujii, Y. Utsunomiya, J. Hiratake, A. Sogabe, K. Sakata, $Biochim.\ Biophys.\ Acta\ Mol.\ Cell.\ Biol.\ Lipids$ 2003, 1631, 197-205; D. Rotticci, T. Norin, K. Hult, M. Martinelle, $Biochim.\ Biophys.\ Acta$ 2000, 1483, 132-140 (which is hereby incorporated by reference herein) with the exception of the use of the fluorophor 4-MU as leaving group instead of the chromophore 4-nitrophenol, improving the inhibitor's stability and lowering the detection limit of the active site titration.

Experimental Procedure: Tetrazole (43.8 μmol, 0.45 M in acetonitrile, 97 μl), methanol (4.38 mmol, 177 μl), and diisopropylethylamine (4.93 mmol, 858 μl) were added to 30 ml toluene under argon. The solution was cooled to 6° C. before adding hexylphosphonic dichloride (4.93 mmol, 844 μl) dropwise. The solution was then warmed to room temperature and stirred for 4 h. 4-MU (4.38 mmol, 0.7712 g) was dissolved in a mixture of toluene (3 ml) and diisopropylethylamine (4.93 mmol, 858 μl) and added to the solution. After stirring the reaction overnight at ambient temperature, the solid was filtered off and washed with toluene and the combined filtrate evaporated. A silica gel column eluted with methylene chloride:ethyl acetate (3:2) and preparative TLC plates with hexane:ethyl acetate (1:1) were used to purify the product, yielding 165 mg (11% yield) of a slightly cloudy liquid. $^1H$ NMR ($CDCl_3$). δ, ppm: 0.89 (t, 3H), 1.30 (m, 4H), 1.42 (m, 2H), 1.69 (m, 2H), 1.94 (m, 2H), 2.43 (s, 3H), 3.83 (d, 3H), 6.25 (s, 1H), 7.18 (s, 1H), 7.23 (d, 1H), 7.57 (d, 1H). $^{13}C$ NMR ($CDCl_3$). δ, ppm: 14.1, 18.9, 22.4, 24.9, 26.3, 30.3, 31.3, 53.2, 109.1, 114.2, 117.1, 117.2, 126.0, 152.1, 153.4, 154.6, 160.7. $^{31}$P NMR (CDCl3). δ, ppm: 29.5.

Active site titration: The amount of active lipase immobilized on resin was determined by active site titration assay. Briefly, stock solution of Methyl 4-methylumbelliferyl hexylphosphonate (30 μl, 0.3 mM in acetonitrile) was diluted with acetonitrile (970 μl) and enzyme-resin (1-15 mg) was added. The reaction was incubated on a head-over-head shaker at ambient temperature for 7 days until the daily fluorescence reading (ex: 360/em: 460 nm) indicated that the reaction had reached equilibrium. The released fluorophor was quantified spectrophotometrically and the amount of active lipase calculated based on the linear relationship between immobilized enzyme and 4-MU in solution.

Kinetic analysis & enantioselectivity of immobilized lipases: The rate of transesterification of chiral alcohols 1-3 with vinylacetate was performed in 2-ml reaction volume containing 1-10 mg of enzyme resin. Product formation was monitored by chiral GC analysis. Specifically, reactions with 2 were performed in cyclohexane at room temperature, using 50 mM internal standard (6-methyl-5-hepten-2-one) and between 25 mM to 1.2 M of substrate. After 30 min preincubation, the reaction was initiated by adding vinyl acetate (200 μl, [final]=1.2 M). At least five samples over a period of 1 to 6 minutes were taken, limiting overall substrate conversions to <5%. The samples were analyzed by GC (G6850-system; Agilent Technologies, Santa Clara, Calif.), using a Cyclosil-B column (length 30 m, i.d. 0.32 mm, film 0.25 mm) connected to a FID. Hydrogen was used as the carrier gas, and the temperature was 75° C. for 30 min. The retention time for S-2 and R-2 was 17.1 min and 15.8 min respectively. Transesterification of R/S-1 with vinyl acetate was performed in acetonitrile. The concentration of the internal standard was lowered to 10 mM. The temperature program for GC analysis was: 65° C. for 5 min, 2° C./min to 90° C., then 10° C./min to 120° C. The retention time for R-1 and S-1 was 15.1 min and 16.9 min respectively. The reaction of R/S-3 with vinyl acetate was also performed in acetonitrile with 10 mM benzophenone as internal standard. The GC temperature program was 160° C. for 40 min. The retention time for S-3 and R3 was 16.5 min and 18.3 min respectively.

The esterification reaction of chiral carboxylates 4 and 5 with 1-propanol was performed in 4-methyl-2-pentanone at 50° C. Each 2-ml reaction mixture contained 10-40 mg enzyme resin, 10 mM 4'-methoxy acetophenone (for 4) or 5 mM benzophenone (for 5) as internal standard, as well as 50-600 mM of substrate. The mixture was preincubated at 50° C. for 30 min and the reaction initiated by addition of 1-propanol ([final]=600 mM). At least five samples over a period of 1 to 6 minutes were taken, limiting overall substrate conversions to <5%. The samples were analyzed by GC, using a HP-1 column (length 30 m, i.d. 0.32 mm, film 0.25 mm) connected to a FID. Hydrogen was used as the carrier gas. For 4, the GC program ran isothermal at 110° C. for 10 min. The retention time for substrate and propyl-ester was 5.4 min and 7.4 min respectively. For 5, the GC program ran isothermal at 170° C. for 30 min. The retention time for substrate and propyl-ester was 10.4 min and 12.8 min respectively.

---

We claim:

1. A circularly permuted protein comprising:
lipase B from Candida Antarctica (CALB);
a linker sequence linking a native amino-terminal end of CALB and a native carboxy-terminal end of CALB; and
a new amino-terminal end and a new carboxy-terminal end, wherein the new amino-terminal and carboxy-terminal ends of the circularly permuted protein are different from the native amino-terminal and carboxy-terminal ends of a corresponding native CALB protein, wherein the new amino-terminal end is located at an amino acid residue corresponding to an amino acid residue of the CALB protein SEQ ID No: 2 selected from: 144, 148, 150, 268, 277, 278, 283, 284, 289, and 294,
wherein the circularly permuted protein comprises at least one improvement over the corresponding native CALB protein, wherein the improvement is selected from: increased activity, increased accessibility to the active site, increased flexibility of the active site, increased the enantioselectivity, and broader or changed substrate specificity.

2. The circularly permuted protein of claim 1, wherein the circularly permuted protein has an active site and wherein, when the circularly permuted protein is in a folded confirmation, the new amino terminal and carboxy terminal ends are located near the active site of the protein.

3. The circularly permuted protein of claim 1, wherein the circularly permuted protein has increased accessibility to the active site over that of the native protein.

4. The circularly permuted protein of claim 3, wherein the increased active site accessibility allows the circularly permuted protein to couple to at least one substrate that the corresponding native protein is substantially unable to couple.

5. The circularly permuted protein of claim 3, wherein the increased active site accessibility broadens or changes the substrate specificity of the circularly permuted protein over that of the corresponding native protein.

6. The circularly permuted protein of claim 1, wherein the circularly permuted protein has increased flexibility to the active site as compared to that of the corresponding native protein.

7. The circularly permuted protein of claim 1, wherein the circularly permuted protein has substantially similar or increased enantioselectivity over that of the corresponding native protein.

8. The circularly permuted protein of claim 1, wherein the circularly permuted protein has increased activity over that of the corresponding native protein.

9. The circularly permuted protein of claim 1, wherein the protein is immobilized to a surface.

10. The circularly permuted protein of claim 9, wherein the protein is immobilized to a matrix material.

11. The circularly permuted protein of claim 9, wherein the immobilization increases the stability of the circularly permuted protein.

12. A circularly permuted protein comprising:
lipase B from Candida Antarctica (CALB) having an original amino acid sequence comprising the amino acid sequence of SEQ ID No: 2;
a linker sequence linking an original amino-terminal end of CALB and an original caboxy-terminal end of CALB; and
a new amino-terminal end and a new carboxy-terminal end, wherein the new amino-terminal and carboxy-terminal ends of the circularly permuted protein of the α/β-hydrolase fold family are different from the original amino-terminal and carboxy-terminal ends of a corresponding native CALB protein, wherein the new amino-terminal end is located in a region of the corresponding native CALB protein selected from: α7, α9, α16 and α17;
wherein the circularly permuted protein comprises at least one improvement over the corresponding native CALB protein, wherein the improvement is selected from: increased activity, increased accessibility to the active site, increased flexibility of the active site, increased the enantioselectivity, and broader or changed substrate specificity.

13. The circularly permuted protein of claim 12, wherein the circularly permuted protein has an active site and wherein, when the circularly permuted protein is in a folded confirmation, the new amino terminal and carboxy terminal ends are located near the active site.

14. The circularly permuted protein of claim 12, wherein the circularly permuted protein has a cap domain corresponding to a cap domain of the native CALB protein and wherein, when the circularly permuted protein is in a folded confirmation, the new amino terminal and carboxy terminal ends are located in the cap domain.

15. The circularly permuted protein of claim 12, wherein the protein has increased accessibility to the active site over that of the native protein.

16. The circularly permuted protein of claim 15, wherein the increased active site accessibility allows the circularly permuted protein to couple to at least one substrate that the corresponding native protein is substantially unable to couple.

17. The circularly permuted protein of claim 15, wherein the increased active site accessibility allows the circularly permuted protein to couple esters and amides.

18. The circularly permuted protein of claim 17, wherein the esters are selected from: esters of primary alcohols, esters of secondary alcohols, and esters of tertiary alcohols.

19. The circularly permuted protein of claim 12, wherein the protein has increased flexibility to the active site as compared to that of the corresponding native protein.

20. The circularly permuted protein of claim 12, wherein the protein has substantially similar or increased enantioselectivity over that of the corresponding native protein.

21. The circularly permuted protein of claim 12, wherein the protein has increased activity over that of the corresponding native protein.

22. The circularly permuted protein of claim 12, wherein the protein is immobilized to a surface.

23. The circularly permuted protein of claim 12, wherein the new amino-terminal end is located at a residue corresponding to an amino acid residue of SEQ ID No: 2 selected from: 144, 148, 150, 193, 268, 277, 278, 283, 284, 289, and 294.

24. The circularly permuted protein of claim 12, wherein the new amino-terminal end is located at a residue corresponding to residue 283 of SEQ ID No: 2.

25. The circularly permuted protein of claim 12, wherein the circularly permuted protein is cp283 having SEQ ID No: 14, wherein cp283 comprises an external loop region comprising the original amino-terminal and carboxy-terminal ends of the corresponding native protein and the linker sequence, and wherein the secondary mutation comprises a deletion of one or more amino acids in the external loop region.

26. The circularly permuted protein of claim 25, wherein the deletion of one or more amino acids in the external loop region results in a second circularly permuted protein, and wherein the second circularly permuted protein has substantially similar or increased activity over cp283 and has increased stability over cp283.

27. A circularly permuted protein comprising:
lipase B from Candida Antarctica (CALB), wherein an original amino-terminal end and an original carboxy-terminal end of CALB have been linked together;
a new amino-terminal end and a new carboxy-terminal end, wherein the new amino-terminal and carboxy-terminal ends of the circularly permuted protein are different from the original amino-terminal and carboxy-terminal ends of a corresponding native CALB protein, wherein the new amino-terminal end is located at an amino acid residue corresponding to an amino acid residue of SEQ ID No: 2 selected from: 144, 148, 150, 268, 277, 278, 283, 284, 289, and 294, wherein the circularly permuted protein comprises at least one improvement over the corresponding native CALB protein, wherein the improvement is selected from: increased activity, increased accessibility to the active site, increased flexibility of the active site, increased the enantioselectivity, and broader or changed substrate specificity.

28. The circularly permuted protein of claim 1, wherein the circularly permuted protein is cp283 comprising SEQ ID No: 14.

29. The circularly permuted protein of claim 1, wherein the new amino-terminal end is located at a residue corresponding to residue 283 of SEQ ID NO: 2.

30. The circularly permuted protein of claim 29, wherein the circularly permuted protein is cp283 having SEQ ID No: 14, wherein cp283 comprises an external loop region comprising the original amino-terminal and carboxy-terminal ends of the corresponding native protein and the linker sequence, and wherein the circularly permuted protein further comprises a secondary mutation comprising a deletion of one or more amino acids in the external loop region.

31. The circularly permuted protein of claim 30, wherein the deletion of one or more amino acids in the external loop region results in a second circularly permuted protein, and wherein the second circularly permuted protein has substantially similar or increased activity over cp283 and has increased stability over cp283.

* * * * *

SEQUENCE LISTING

<160> NUMBER OF SEQ ID NOS: 29

<210> SEQ ID NO 1
<211> LENGTH: 954
<212> TYPE: DNA
<213> ORGANISM: Candida antarctica

<400> SEQUENCE: 1

```
ctaccttccg gttcggaccc tgccttttcg cagcccaagt cggtgctcga tgcgggtctg      60
acctgccagg gtgcttcgcc atcctcggtc tccaaaccca tccttctcgt ccccggaacc     120
ggcaccacag gtccacagtc gttcgactcg aactggatcc ccctctctgc gcagctgggt     180
tacacaccct gctggatctc accccgccg ttcatgctca acgacaccca ggtcaacacg      240
gagtacatgg tcaacgccat caccacgctc tacgctggtt cgggcaacaa caagcttccc     300
gtgctcacct ggtcccaggg tggtctggtt gcacagtggg gtctgacctt cttcccagt      360 atcaggtcca aggtcgatcg acttatggcc tttgcgcccg actacaaggg caccgtcctc     420
gccggccctc tcgatgcact cgcggttagt gcaccctccg tatggcagca aaccaccggt     480
tcggcactca ctaccgcact ccgaaacgca ggtggtctga cccagatcgt gcccaccacc     540
aacctctact cggcgaccga cgagatcgtt cagcctcagg tgtccaactc gccactcgac     600
tcatcctacc tcttcaacgg aaagaacgtc caggcacagg ctgtgtgtgg gccgctgttc     660
gtcatcgacc atgcaggctc gctcacctcg cagttctcct acgtcgtcgg tcgatccgcc     720
ctgcgctcca ccacgggcca ggctcgtagt gcagactatg gcattacgga ctgcaaccct     780
cttcccgcca atgatctgac tcccgagcaa aaggtcgccg cggctgcgct cctggcgccg     840
gcggctgcag ccatcgtggc gggtccaaag cagaactgcg agcccgacct catgccctac     900 gcccgccct ttgcagtagg caaaaggacc tgctccggca tcgtcacccc ctaa            954
```

```
<210> SEQ ID NO 2
<211> LENGTH: 317
<212> TYPE: PRT
<213> ORGANISM: Candida antarctica

<400> SEQUENCE: 2

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Ala Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315

<210> SEQ ID NO 3
<211> LENGTH: 6
<212> TYPE: PRT
<213> ORGANISM: Artificial Sequence
<220> FEATURE:
<223> OTHER INFORMATION: Linker Sequence

<400> SEQUENCE: 3

Gly Gly Thr Ser Gly Gly
1               5
```

```
<210> SEQ ID NO 4
<211> LENGTH: 18
<212> TYPE: DNA
<213> ORGANISM: Artificial Sequence
<220> FEATURE:
<223> OTHER INFORMATION: Linker Sequence

<400> SEQUENCE: 4
ggcggtacta gtggtggc                                                        18

<210> SEQ ID NO 5
<211> LENGTH: 72
<212> TYPE: DNA
<213> ORGANISM: Artificial Sequence
<220> FEATURE:
<223> OTHER INFORMATION: Primer Sequence, ZQ_CALBfor1

<400> SEQUENCE: 5
gaggctgaag ctcatcatca tcatcatcat agcagcggcc ttgttccacg tctaccttcc          60
ggttcggacc ct                                                              72

<210> SEQ ID NO 6
<211> LENGTH: 45
<212> TYPE: DNA
<213> ORGANISM: Artificial Sequence
<220> FEATURE:
<223> OTHER INFORMATION: Primer Sequence, ZG_CALBfor2

<400> SEQUENCE: 6
cgcctcgaga aaagagaggc tgaagctcat catcatcatc atcat                          45

<210> SEQ ID NO 7
<211> LENGTH: 35
<212> TYPE: DNA
<213> ORGANISM: Artificial Sequence
<220> FEATURE:
<223> OTHER INFORMATION: Primer Sequence, ZQ_CALBrev

<400> SEQUENCE: 7
cgcgcggccg cttaggggt gacgatgccg gagca                                      35

<210> SEQ ID NO 8
<211> LENGTH: 36
<212> TYPE: DNA
<213> ORGANISM: Artificial Sequence
<220> FEATURE:
<223> OTHER INFORMATION: Primer Sequence, ZQ_cpCALBfor

<400> SEQUENCE: 8
ggtactagtg gtggcctacc ttccggttcg gaccct                                    36

<210> SEQ ID NO 9
<211> LENGTH: 36
<212> TYPE: DNA
<213> ORGANISM: Artificial Sequence
<220> FEATURE:
<223> OTHER INFORMATION: Primer Sequence, ZQ_cpCALBrev

<400> SEQUENCE: 9
cgcactagta ccgccggggg tgacgatgcc ggagca                                    36

<210> SEQ ID NO 10
<211> LENGTH: 36
<212> TYPE: DNA
<213> ORGANISM: Artificial Sequence
<220> FEATURE:
<223> OTHER INFORMATION: Primer Sequence, ZQ_pAMBfor
```

-continued

```
<400> SEQUENCE: 10
ccggatatca ggccttggaa caaggccgct gctatg                                36

<210> SEQ ID NO 11
<211> LENGTH: 33
<212> TYPE: DNA
<213> ORGANISM: Artificial Sequence
<220> FEATURE:
<223> OTHER INFORMATION: Primer Sequence, ZQ_pAMBrev

<400> SEQUENCE: 11
ccggatatct tataagcggc cgcaagcttg tcg                                   33

<210> SEQ ID NO 12
<211> LENGTH: 21
<212> TYPE: DNA
<213> ORGANISM: Artificial Sequence
<220> FEATURE:
<223> OTHER INFORMATION: Primer Sequence, ZQ-pPIC9-for

<400> SEQUENCE: 12
tactattgcc agcattgctg c                                                21

<210> SEQ ID NO 13
<211> LENGTH: 21
<212> TYPE: DNA
<213> ORGANISM: Artificial Sequence
<220> FEATURE:
<223> OTHER INFORMATION: Primer Sequence, ZQ-pPIC9-rev

<400> SEQUENCE: 13
gcaaatggca ttctgacatc c                                                21

<210> SEQ ID NO 14
<211> LENGTH: 323
<212> TYPE: PRT
<213> ORGANISM: Artificial Sequence
<220> FEATURE:
<223> OTHER INFORMATION: cp283, a circular permutation of lipase B from
      Candida antarctica, SEQ ID NO: 2

<400> SEQUENCE: 14
```

Ala Ala Ile Val Ala Gly Pro Lys Gln Asn Cys Glu Pro Asp Leu Met
1               5                   10                  15

Pro Tyr Ala Arg Pro Phe Ala Val Gly Lys Arg Thr Cys Ser Gly Ile
            20                  25                  30

Val Thr Pro Gly Gly Thr Ser Gly Leu Pro Ser Gly Ser Asp Pro
        35                  40                  45

Ala Phe Ser Gln Pro Lys Ser Val Leu Asp Ala Gly Leu Thr Cys Gln
    50                  55                  60

Gly Ala Ser Pro Ser Ser Val Ser Lys Pro Ile Leu Leu Val Pro Gly
65                  70                  75                  80

Thr Gly Thr Thr Gly Pro Gln Ser Phe Asp Ser Asn Trp Ile Pro Leu
                85                  90                  95

Ser Ala Gln Leu Gly Tyr Thr Pro Cys Trp Ile Ser Pro Pro Pro Phe
            100                 105                 110

Met Leu Asn Asp Thr Gln Val Asn Thr Glu Tyr Met Val Asn Ala Ile
        115                 120                 125

Thr Thr Leu Tyr Ala Gly Ser Gly Asn Asn Lys Leu Pro Val Leu Thr
    130                 135                 140

Trp Ser Gln Gly Gly Leu Val Ala Gln Trp Gly Leu Thr Phe Phe Pro
145                 150                 155                 160

```
Ser Ile Arg Ser Lys Val Asp Arg Leu Met Ala Phe Ala Pro Asp Tyr
            165                 170                 175

Lys Gly Thr Val Leu Ala Gly Pro Leu Asp Ala Leu Ala Val Ser Ala
        180                 185                 190

Pro Ser Val Trp Gln Gln Thr Thr Gly Ser Ala Leu Thr Ala Leu
        195                 200                 205

Arg Asn Ala Gly Gly Leu Thr Gln Ile Val Pro Thr Thr Asn Leu Tyr
        210                 215                 220

Ser Ala Thr Asp Glu Ile Val Gln Pro Gln Val Ser Asn Ser Pro Leu
225                 230                 235                 240

Asp Ser Ser Tyr Leu Phe Asn Gly Lys Asn Val Gln Ala Gln Ala Val
            245                 250                 255

Cys Gly Pro Leu Phe Val Ile Asp His Ala Gly Ser Leu Thr Ser Gln
            260                 265                 270

Phe Ser Tyr Val Val Gly Arg Ser Ala Leu Arg Ser Thr Thr Gly Gln
            275                 280                 285

Ala Arg Ser Ala Asp Tyr Gly Ile Thr Asp Cys Asn Pro Leu Pro Ala
        290                 295                 300

Asn Asp Leu Thr Pro Glu Gln Lys Val Ala Ala Ala Leu Leu Ala
305                 310                 315                 320

Pro Ala Ala

<210> SEQ ID NO 15
<211> LENGTH: 37
<212> TYPE: PRT
<213> ORGANISM: Artificial Sequence
<220> FEATURE:
<223> OTHER INFORMATION: amino acids 6-42 of cp283D11, a variant of SEQ
      ID NO: 14

<400> SEQUENCE: 15

Gly Pro Lys Gln Asn Cys Glu Pro Asp Leu Met Pro Tyr Ala Arg Pro
1               5                   10                  15

Phe Ala Val Gly Lys Arg Ser Gly Gly Leu Pro Ser Gly Ser Asp Pro
            20                  25                  30

Ala Phe Ser Gln Pro
        35

<210> SEQ ID NO 16
<211> LENGTH: 37
<212> TYPE: PRT
<213> ORGANISM: Artificial Sequence
<220> FEATURE:
<223> OTHER INFORMATION: amino acids 6-42 of cp283D11a, a variant of SEQ
      ID NO: 14

<400> SEQUENCE: 16

Gly Pro Lys Gln Asn Cys Glu Pro Asp Leu Met Pro Tyr Ala Arg Pro
1               5                   10                  15

Phe Ala Val Gly Lys Arg Thr Gly Gly Leu Pro Ser Gly Ser Asp Pro
            20                  25                  30

Ala Phe Ser Gln Pro
        35

<210> SEQ ID NO 17
<211> LENGTH: 38
<212> TYPE: PRT
<213> ORGANISM: Artificial Sequence
<220> FEATURE:
<223> OTHER INFORMATION: amino acids 6-43 for cp283D10 of Lipase B from
      Candida antarctica
```

-continued

```
<400> SEQUENCE: 17

Gly Pro Lys Gln Asn Cys Glu Pro Asp Leu Met Pro Tyr Ala Arg Pro
1               5                   10                  15

Phe Ala Val Gly Lys Arg Thr Cys Gly Gly Leu Pro Ser Gly Ser Asp
            20                  25                  30

Pro Ala Phe Ser Gln Pro
            35

<210> SEQ ID NO 18
<211> LENGTH: 40
<212> TYPE: PRT
<213> ORGANISM: Artificial Sequence
<220> FEATURE:
<223> OTHER INFORMATION: amino acids 6-45 of cp283D8 of Lipase B from
      Candida antarctica

<400> SEQUENCE: 18

Gly Pro Lys Gln Asn Cys Glu Pro Asp Leu Met Pro Tyr Ala Arg Pro
1               5                   10                  15

Phe Ala Val Gly Lys Arg Thr Cys Ser Ser Gly Gly Leu Pro Ser Gly
            20                  25                  30

Ser Asp Pro Ala Phe Ser Gln Pro
            35                  40

<210> SEQ ID NO 19
<211> LENGTH: 41
<212> TYPE: PRT
<213> ORGANISM: Artificial Sequence
<220> FEATURE:
<223> OTHER INFORMATION: amino acids 6-46 of cp283D7 of Lipase B from
      Candida antarctica

<400> SEQUENCE: 19

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Gly Gly Leu Pro Ser
            20                  25                  30

Gly Ser Asp Pro Ala Phe Ser Gln Pro
            35                  40

<210> SEQ ID NO 20
<211> LENGTH: 41
<212> TYPE: PRT
<213> ORGANISM: Artificial Sequence
<220> FEATURE:
<223> OTHER INFORMATION: amino acids 6-46 of cp283D7a of Lipase B from
      Candida antarctica

<400> SEQUENCE: 20

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Ser Leu Pro Ser
            20                  25                  30

Gly Ser Asp Pro Ala Phe Ser Gln Pro
            35                  40

<210> SEQ ID NO 21
<211> LENGTH: 43
<212> TYPE: PRT
<213> ORGANISM: Artificial Sequence
<220> FEATURE:
<223> OTHER INFORMATION: amino acids 6-48 of cp283D5 of Lipase B from
      Candida antarctica
```

<400> SEQUENCE: 21

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Thr Pro Gly Leu
            20                  25                  30

Pro Ser Gly Ser Asp Pro Ala Phe Ser Gln Pro
        35                  40

<210> SEQ ID NO 22
<211> LENGTH: 45
<212> TYPE: PRT
<213> ORGANISM: Artificial Sequence
<220> FEATURE:
<223> OTHER INFORMATION: amino acids 6-50 of cp283D3 of Lipase B from
      Candida antarctica

<400> SEQUENCE: 22

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Thr Pro Gly Gly
            20                  25                  30

Thr Leu Pro Ser Gly Ser Asp Pro Ala Phe Ser Gln Pro
        35                  40                  45

<210> SEQ ID NO 23
<211> LENGTH: 46
<212> TYPE: PRT
<213> ORGANISM: Artificial Sequence
<220> FEATURE:
<223> OTHER INFORMATION: amino acids 6-51 of cp283D2 of Lipase B from
      Candida antarctica

<400> SEQUENCE: 23

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Thr Pro Gly Gly
            20                  25                  30

Thr Ser Leu Pro Ser Gly Ser Asp Pro Ala Phe Ser Gln Pro
        35                  40                  45

<210> SEQ ID NO 24
<211> LENGTH: 51
<212> TYPE: PRT
<213> ORGANISM: Artificial Sequence
<220> FEATURE:
<223> OTHER INFORMATION: Primer Sequence

<400> SEQUENCE: 24

Cys Gly Cys Cys Thr Cys Gly Ala Gly Ala Ala Ala Gly Ala Gly
1               5                   10                  15

Ala Gly Gly Cys Thr Gly Ala Cys Ala Gly Cys Thr Cys Thr Ala Cys Cys
            20                  25                  30

Thr Thr Cys Cys Gly Gly Thr Thr Cys Gly Gly Ala Cys Cys Cys Thr
        35                  40                  45

Gly Cys Cys
    50

<210> SEQ ID NO 25
<211> LENGTH: 43
<212> TYPE: PRT
<213> ORGANISM: Artificial Sequence

```
<220> FEATURE:
<223> OTHER INFORMATION: amino acids 6-49 for cp283D4 of Liapse B from
      Candida antarctica

<400> SEQUENCE: 25

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Thr Pro Gly Gly
            20                  25                  30

Leu Pro Gly Ser Asp Pro Ala Phe Ser Gln Pro
        35                  40

<210> SEQ ID NO 26
<211> LENGTH: 44
<212> TYPE: PRT
<213> ORGANISM: Artificial Sequence
<220> FEATURE:
<223> OTHER INFORMATION: amino acids 6-49 for cp283D4a of Liapse B from
      Candida antarctica

<400> SEQUENCE: 26

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Thr Pro Gly Gly
            20                  25                  30

Thr Pro Ser Gly Ser Asp Pro Ala Phe Ser Gln Pro
        35                  40

<210> SEQ ID NO 27
<211> LENGTH: 46
<212> TYPE: PRT
<213> ORGANISM: Artificial Sequence
<220> FEATURE:
<223> OTHER INFORMATION: amino acids 6-51 for cp283D2a of Lipase B from
      Candida antarctica

<400> SEQUENCE: 27

Gly Pro Lys Gln Asn Cys Glu Pro Asp Leu Met Pro Tyr Ala Arg Pro
1               5                   10                  15

Phe Ala Val Gly Lys Arg Thr Cys Ser Gly Ile Val Thr Pro Gly Gly
            20                  25                  30

Thr Ser Ala Pro Ser Gly Ser Asp Pro Ala Phe Ser Gln Pro
        35                  40                  45

<210> SEQ ID NO 28
<211> LENGTH: 23
<212> TYPE: DNA
<213> ORGANISM: Artificial Sequence
<220> FEATURE:
<223> OTHER INFORMATION: Primer Sequence

<400> SEQUENCE: 28
gagctccgtc gacaagcttg cgg                                          23

<210> SEQ ID NO 29
<211> LENGTH: 24
<212> TYPE: DNA
<213> ORGANISM: Artificial Sequence
<220> FEATURE:
<223> OTHER INFORMATION: Primer Sequence

<400> SEQUENCE: 29
ggatgagcat tcatcaggcg ggca                                         24
```